US007282599B2

(12) United States Patent
Gaudernak et al.

(10) Patent No.: US 7,282,599 B2
(45) Date of Patent: Oct. 16, 2007

(54) DITHIOCARBAMATE ANTIVIRAL AGENTS AND METHODS OF USING SAME

(75) Inventors: Elisabeth Gaudernak, Vienna (AT); Andreas Grassauer, Vienna (AT); Ernst Küchler, Vienna (AT); Thomas Muster, Vienna (AT); Joachim Seipelt, Vienna (AT)

(73) Assignee: Avir Green Hills Biotechnology Research Devlopment Trade AG, Vienna (AT)

( * ) Notice: Subject to any disclaimer, the term of this patent is extended or adjusted under 35 U.S.C. 154(b) by 76 days.

(21) Appl. No.: 10/483,975

(22) PCT Filed: Jul. 15, 2002

(86) PCT No.: PCT/AT02/00206

§ 371 (c)(1),
(2), (4) Date: Aug. 18, 2004

(87) PCT Pub. No.: WO03/007935

PCT Pub. Date: Jan. 30, 2003

(65) Prior Publication Data

US 2006/0069153 A1 Mar. 30, 2006

(30) Foreign Application Priority Data

Jul. 16, 2001 (AT) .............................. A 1102/2001
Jul. 16, 2001 (AT) .............................. A 1103/2001
Dec. 17, 2001 (AT) .............................. A 1972/2001
Dec. 17, 2001 (AT) .............................. A 1973/2001

(51) Int. Cl.
*C07C 333/00* (2006.01)
*C12Q 1/70* (2006.01)
(52) U.S. Cl. ......................................... 558/232; 435/5
(58) Field of Classification Search .................... 435/5; 558/232
See application file for complete search history.

(56) References Cited

U.S. PATENT DOCUMENTS

| 5,686,436 A | 11/1997 | Van Dyke ................... 514/171 |
| 6,093,743 A | 7/2000 | Lai et al. ..................... 514/599 |

FOREIGN PATENT DOCUMENTS

| DE | 1963223 | 12/1969 |
| DE | 2555730 | 6/1976 |
| GB | 861043 | * 2/1961 |
| JP | 51139632 | 12/1976 |
| WO | WO95/03792 | 2/1995 |
| WO | WO96/10402 | 4/1996 |
| WO | WO99/08665 | 2/1999 |
| WO | WO99/64068 | 12/1999 |
| WO | WO99/66918 | 12/1999 |
| WO | WO 01/51046 | 7/2001 |

OTHER PUBLICATIONS

Elisabeth Gaudernak, Joachim Seipelt, Andrea Triendl, Andreas Grassauer, and Ernst Kuechler Antiviral Effects of Pyrrolidine Dithiocarbamate on Human Rhinoviruses Journal of Virology, Jun. 2002, p. 6004-6015, vol. 76, No. 12.*
Jay G Calvert and Edward H Simon Effects of the Copper Chelators Diethyldithiocarbamate and Bathocuproine Sulfonate on Interferon and Its Antiviral State Journal of Interferon Research 10:13-23 (1999).*
Baum and Paulson, "Sialyloligosaccharides of the respiratory epithelium in the selection of human influenza virus receptor specificity," *Acta Histochemica*, Suppl., S35-38, 1990.
Calvert, "Effects of the copper chelators diethyldithiocarbamate and bathocuproine sulfonate on interferon and its antiviral state," *Interferon Research*, 10:13-23, 1990.
Dollery, In: *Therapeutic Drugs*, Second Ed., vol. 1, Churchill Livingstone, Edinburgh, 1999.
Fields et al., In: *Virology*, 3rd Edition, Lippencott-Raven Publ., Philadelphia, vol. 1, 434-436, 1995.
Flory et al., "Influenza virus-induced NF-κB-dependent gene expression is mediated by overexpression of viral proteins and involves oxidative radicals and activationof IκB kinase," *J. Biol. Chem.*, 275(12):8307-8314, 2000.
Gorman et al., "Evolution of influenza A virus nucleoprotein genes: implications for the origins of H1N1 human and classical swine viruses," *J. Virol.*, 65(7):3704-3714, 1991.
Grambas and Hay, Maturation of influenza A virus hemagglutinin-estimates of the pH encountered during transport and its regulation by the M2 protein, *Virology*, 190:11-18, 1992.
Grambas et al., "Influence of amantadine resistance mutations on the pH regulatory function of the M2 protein of influenza A viruses," *Virology*, 191:541-549, 1992.
Hinshaw and Webser, "The perpetuation of orthomyxoviruses and paramyoxviruses in Canadian waterfowl," *Can. J. Microbiol.*, 26:622-629, 1980.
Knobil et al., "Role of oxidants in influenza virus-induced gene expression," *Am. J. Physiol.*, 274(1):134-142, 1998.
Ludwig et al., "European swine virus as a possible source for the next influenza pandemic?" *Virology*, 212:555-561, 1995.

(Continued)

*Primary Examiner*—Johann R Richter
*Assistant Examiner*—Lalitha Nagubandi
(74) *Attorney, Agent, or Firm*—Fulbright & Jaworski, LLP

(57) ABSTRACT

The invention discloses a use of dithiocarbamate compounds having the structural formula $R_1R_2NCS_2H$, in which $R_1$ and $R_2$, independently of each other, represent a straight or branched $C_1$-$C_4$ alkyl, or, with the nitrogen atom, form an aliphatic ring with 4 to 6 C atoms, in which $R_1$, $R_2$, or the aliphatic ring is optionally substituted with one or more substituents selected from OH, $NO_2$, $NH_2$, COOH, SH, F, Cl, Br, I, methyl or ethyl, and oxidized forms of these compounds, in particular dimers thereof, as well as pharmaceutically acceptable salts thereof, to prepare an agent for treating or preventing an infection by RNA viruses which attack the respiratory tract and cause disease there.

17 Claims, 16 Drawing Sheets

OTHER PUBLICATIONS

Meyer et al., "H2O2 and antioxidants have opposite effects on activation of NF-κB and AP-1 in intact cells: AP-1 as secondary antioxidant-responsive factor," *EMBO J.*, 12:2005-2015, 1993.

Rogers and Paulson, "Receptor determinants of human and animal influenza virus isolates: differences in receptor specificity of the H3 hemagglutinin based on species of origin," *Virology*, 127:361-373, 1983.

Schwarz et al., "Nf-κB-mediated inhibition of apoptosis is required for encephalomyocarditis virus virulence: a mechanism of resistance in p50 knockout mice," *J. Virology*, 72(7):5654-5660, 1998.

Sherman et al., "Pyrrolidine dithiocarbamate inhibits induction of nitirc oxide synthase activity in rat alveolar macrophages," *Biochem. Biophys. Res. Comm.*, 191(3):1301-1308, 1993.

Tai et al., "Activation of nuclear factor κB in hepatitis C virus infection: implications for pathogenesis and hepatocarcinogenesis," *Hepatology*, 31(3):656-664, 2000.

The HIV87 Study Group. "Multicenter, randomized, placebo-controlled study of ditiocarb (Imuthiol) in human immunodeficiency virus-infected asymptomatic and minimally symptomatic patients," *AIDS Res Hum Retroviruses*; 9:83-89, 1993.

*Virus Taxonomy: The Classification and Nomenclature of Viruses. The Seventh Report of the International Committee on Taxonomy of Viruses*, Regenmortet et al. (ed.), Academic Press, SanDiego, 657-673, 2000.

Yen, "Nuclear factor κB and hepatitis C-is there a connection?", *Hepatology*, 31(3):785-787, 2000.

\* cited by examiner

|  | − PDTC | + PDTC |
|---|---|---|
| n.i. |  |  |
| 8h p.I. HRV-14 |  |  |

DITHIOCARBAMATE ANTIVIRAL AGENTS AND METHODS OF USING SAME

This application is a U.S. national phase application under 35 U.S.C. § 371 of International Application No. PCT/AT02/00206 filed 15 Jul. 2002, which claims priority to Austrian Applications No. A 1103/01 filed 16 Jul. 2001, No. A 1102/01 filed 16 Jul. 2001, No. A 1973/01 filed 17 Dec. 2001, and No. A 1972/01 filed 17 Dec. 2001, the disclosures of each of which are incorporated herein in their entirety.

The invention concerns the use of dithiocarbamate compounds as well as a disinfectant and a process for disinfecting surfaces, media or cell cultures.

There are many viruses which cause diseases in the respiratory tract of humans and mammals. Although these respiratory-pathogenic viruses can differ structurally and belong to different virus families, they all have in common that they can penetrate into the body through the respiratory tract by, for instance, attacking specific cells in that tract, such as the epithelial cell layer in the respiratory tract, alveolar cells, lung cells, etc. The classical symptoms of flu are common to all of them, which flu is characterized by local inflammation and disease symptoms in the respiratory tract (such as a runny nose, hoarseness, coughing, vesicles, sore throat).

Viral infections, particularly in the respiratory tract, produce pathological changes in the cells affected through oxidative stress, especially in epithelial cells. Reactive oxygen intermediates (ROIs), such as are produced by leukocytes, epithelial pulmonary cells or xanthine oxidases, are considered mediators of these virus-induced cell injuries. Activation of the oxidant-specific transcription factor NFκKB (Nuclear Factor κB) can occur in the course of this oxidative stress. NFκB has been found in the most varied cell types and has been related to activation of genes for inflammatory and immune responses.

Antioxidants can block activation of NFκB by trapping the ROIs, which, otherwise, would cause such activation. Therefore, the use of antioxidants has been proposed, especially for treatment of infections with latent viruses. It has been found, though, that these latent infections cannot be treated effectively with single antioxidants alone, rather, they can be treated effectively, if at all, only by combined therapy using a mixture of different antioxidants (i. e., antioxidants having different actions) and other virus-inhibiting substances (U.S. Pat. No. 5,686,436).

It has not yet been possible to attain inhibition of viral replication, or even of virus infection, by antioxidants, and especially not of infections with influenza or picorna viruses (Knobil et al., Am. J. Physiol. 274 (1) (1998) (134-142).

On the other hand, the various antioxidants proposed for combatting virus infections are very different in their antioxidative activities. For instance, L-ascorbic acid and Vitamin E serve for the protection of glutathione; Vitamins K, A and E act as antagonists of peroxynitrite and other strong oxidants in the body. Anti-inflammatory steroids, non-glucocorticoidal lazaroids, dithiocarbamates and N-acetyl-L-cysteine have been described as inhibitors of NFκB activation.

Viruses can be classified as DNA or RNA viruses, depending on their carrier of genetic information, the nucleic acid being single-stranded or double-stranded and surrounded by a protein envelope.

The single-stranded RNA of these RNA viruses occurs either as the plus-strand (mRNA) or the minus strand. This virus genetic information can also occur in several segments, as in the case of the influenza virus.

The human rhinoviruses (HRV) classified in the picornaviruses are the principal cause of the worldwide common cold. The frequent occurrence of HRV, the risk of severe secondary infections, and the economic effect of medical costs, visits to physicians, and sickness-leaves of employees make HRVs major pathogens, which should be taken seriously. In spite of their frequent occurrence, at this time, there is no reliable treatment for this viral disease other than symptomatic treatment. On the other hand, the consequences of a rhinovirus infection, for instance, are not so serious or even life threatening that it is acceptable to take medications having a high risk of side effects. Therefore, agents to be used against such viruses must exhibit little or no side effects. The group of animal picornaviruses includes the equine rhinitis A virus (ERAV), which, like foot and mouth disease virus (FMV), belongs to the genus of the aphthoviruses.

Other important virus families responsible for diseases in the respiratory tract include the orthomyxoviridae and paramyxoviridae, with human influenza virus as the most important representative.

The occurrence of new pandemic influenza strains, usually, is considered due to new subtypes containing a new hemagglutinin or neuraminidase gene. These new viruses differ immunologically from previously circulating influenza viruses. Influenza A and B viruses require 8 RNA segments to be infectious, while Influenza C viruses need only 7. Influenza A, B and C viruses can produce homotypic reassortants in vivo, but not between the types. In theory, 256 reassortants could be produced from the 8 segments of two Influenza viruses; but such random segregation does not occur because some proteins require their strain specific partner at the protein level. That was demonstrated particularly clearly for the Avian Influenza Virus A/chicken/Germany/34 (H7N1) FPV Rostock HA, which is coded by segment 4, which can form a functional virus specifically only with its strain specific M2 protein, which is coded by segment 7. (Grambas, S., Hay, A. J., Maturation of Influenza A virus hemagglutinin—estimates of the pH encountered during transport and its regulation by the M2 protein; Virology 1992; 190:11-18) (Grambas, S., Bennett, H. S., Hay, A. J., Influence of amantadine resistance mutations on the pH regulatory function of the M2 protein of Influenza A viruses. Virology 1992; 191:541-549). Influenza inoculation is one of the principal strategies against the annual influenza virus infection in the population. Nevertheless, influenza is still a cause of morbidity and mortality in the world and a principal cause of sickness and death in patients with weak immune systems and in older persons. The antiviral activity of Amantadine and Rimantadine reduces the duration of the symptoms of clinical influenza, but important side effects and appearance of resistant mutants have been described (Fields et al., Virology, $3^{rd}$ Edition (1995), Lippincott-Raven Publ., Philadelphia, Vol. 1, p. 434-436). At present, a new group of antiviral agents, which inhibit influenza virus neuraminidase is on the market. Zanamivir and Oseltamivir are examples of inhibitors of influenza A and B virus neuraminidase. However, these medications only reduce the duration of the symptoms.

A process for suppressing the propagation of retroviruses and latent viruses, such as HIV, in humans is described in U.S. Pat. No. 5,686,436. In that process, a medication containing, among other ingredients, antioxidants and NFκB induction inhibitors is administered. In contrast, for effective action against infections with respiratory viruses, the virus must be attacked while it is still in the acute infection phase. This is a treatment that can be used only on the level of the latent viruses and is not suitable to prevent or treat acute viral infections in the respiratory tract.

Thus, there is a need for a highly effective substance that is active against virus infections in the respiratory tract, especially in humans, which causes few if any side effects, is cost-effective, and can be produced in large quantities.

The object of the present invention is attained by using dithiocarbamate compounds having the structural formula $R_1R_2NCS_2H$, in which $R_1$ and $R_2$, independently of each other, represent a straight or branched $C_1$-$C_4$ alkyl, or, with the nitrogen atom, form an aliphatic ring with 4 to 6 C atoms, in which $R_1$, $R_2$, or the aliphatic ring is optionally substituted with one or more substituents selected from OH, $NO_2$, $NH_2$, COOH, SH, F, Cl, Br, I, methyl or ethyl, and oxidized forms of these compounds, in particular dimers thereof, as well as pharmaceutically acceptable salts thereof, to prepare an agent for treating or preventing an infection by RNA viruses, which attack the respiratory tract and cause disease there. In the invention, 'respiratory tract' means all the organs and regions from the body openings (nose, mouth, eyes (including the tear ducts) and ears) to the pulmonary alveoli. Here, the pharmaceutically acceptable salts, in particular, are Na, K, Ca, Mg, $NH_4$ and Zn. It has now been found, surprisingly, and for the first time that the inventive dithiocarbamate compounds can be used effectively against infections by RNA viruses, which attack the respiratory tract and cause disease there; these viruses are called "respiratory RNA viruses" in this application. Contrary to the observations of Knobil et al., (Am. J. Physiol. (1998), pages 134-142), in the scope of the present invention, an antiviral action of the inventive dithiocarbamate compounds against infections with respiratory RNA viruses, such as HRV and influenza infections, could clearly be shown. This is particularly surprising because other antioxidants do not exhibit this antiviral action against respiratory RNA viruses, and the change of the redox potential is not solely responsible for the antiviral action of the dithiocarbamate compounds according to the invention. For example, it can clearly be shown according to the invention that the antioxidants Vitamin C, Vitamin E, 2-mercaptoethanol and N-acetyl-L-cysteine have no action at all against respiratory RNA viruses. Furthermore, the effectiveness of the inventive dithiocarbamate compounds against infections with respiratory RNA viruses and the propagation of these viruses cannot be ascribed solely to inhibition of NFKB activation, much rather, it has been shown that the inventive dithiocarbamate compounds, which are understood to include even the oxidized forms, in the present application, and especially the dimers, specifically prevent propagation of respiratory RNA viruses.

DE 19 63 223 A concerns an agent for treating virus infections in the brain, in which the agent is said to involve an inhibitor of biosynthesis of the monoamines noradrenalin, dopamine and 5-hydroxytryptamine. The example presented in this document shows the action of α-methyltyrosine methyl ester on mice infected with Herpes simplex. Thus, the mechanism of inhibition of the biosynthesis of specific monoamines described in this document is applicable solely to treatment of DNA virus infections in the brain. The treatment of respiratory RNA viruses by the invention acts according to another principle and is not applicable to virus infections in the brain, as shown by the negative examples for FSME (Example 13) and EMC (Example 14). Thus, DE 19 63 223 A concerns a different area of application, and it cannot be compared with the application according to this invention, and thus does not make it obvious, either.

The action of diethyldithiocarbamate on mengoviruses is described in Calvert, J. G., Interferon Research, 1990 (10), page 13-23. It was found there that DDTC inactivates mengovirus virions. Mengoviruses, however, are agents of a severe encephalomyocarditis, and do not affect the respiratory tract or cause disease there.

WO 95/03792 A1 concerns the use of thiol compounds for production of a pharmaceutical composition for treatment of virus-induced diseases, with which disulfide bridges in the virus protein are destroyed by the thiol compound. This document mentions many viruses, including RNA viruses, Picornaviridae among others. The document also gives many examples of thiol compounds, including dithiocarbamate, quite generally. Only the following examples were shown from the many different potential combinations: as thiol compounds, N-acetylcysteine (NAC), cysteine, cysteine hydrochloride and N, S-diacetylcysteine ethyl ester (DACEE). Only hepatitis B and vaccinia virus were shown as virus diseases.

Thus, not only were no examples shown for the majority of the compounds and virus diseases; but it has also turned out that the treatment disclosed in that document does not operate to the extent described: many picornaviruses (those which do not attack the respiratory tract, but nerve cells) are not inhibited by PDTC, and their propagation is not reduced. Thus, not all combinations of virus induced diseases and thiol compounds are successful, and the use of selected dithiocarbamate compounds selected according to the invention—those not disclosed in WO 95/03792 A1—is not made obvious for treatment or prevention of infection by respiratory RNA viruses.

GB 861 043 A concerns compositions, which are used for, among other things, protection against viruses. Those compositions include dithiocarbamates, for instance, but no specific viruses are disclosed there.

Knobil et al., Am. J. Physiol. (1998), pages 134-142, concerns a study of oxidants and their effect on virus induced gene expression. There, though, it was explicitly found that neither NAC nor PDTC inhibits influenza virus infection or replication.

An antimicrobial agent comprising a dimethyldithiocarbamate compound is described in DE 25 55 730 A. This compound is a complex of 8-hydroxyquinoline—metal—N, N-dimethyldithiocarbamate. But that document discloses only fungicidal and antibacterial action.

WO 99/66918 A1 concerns the use of disulfide derivatives of dithiocarbamates to reduce nitrogen oxides in a patient, or to inhibit NFκB. In that document, although a very large number of diseases is reported, the viral diseases are not described specifically.

Flory et al., J. Biol. Chem., 24 Mar. 2000, 275 (12), pages 8307-8314, concerns a study of the effects of various influenza A virus proteins on activation of the NFκB-dependent expression.

Tai, D. I., et al., Hepatology, March 2000, 31 (3), pages 785-787, concerns a study of inhibition of NKFB activation by PDTC, in which it is assumed that an HCV infection could produce anti-apoptosis by activation of NFκB.

Schwarz et al., 1998 (J. Virol; Vol. 72 (7); pages 5654-5660) studied the effect of NFκB on propagation of the encephalomyocarditis virus (EMCV) related to human rhinovirus. In cells without NFκB (knockout p50-/- or p65-/-) infected with EMCV, virus propagation, indeed, is reduced, but apoptotic cell death is increased. That is in strong contrast to the data presented here: these examples can show clearly that the dithiocarbamate compounds according to the invention prevent not only replication of the related rhinovirus, but also the virus induced cell death. Therefore, according to the invention, the inhibition of NFκB is not the critical factor in the effectiveness of the dithiocarbamate compounds.

Neither is the inventive antiviral action of the inventive dithiocarbamate compounds dependent on a combination of particular substances. The inventive dithiocarbamate compounds can be used completely alone, independent of the further additives, especially antioxidants, as is absolutely essential according to U.S. Pat. No. 5,686,436 for an anti-retrovirus action of NFκB-activation inhibitors, because, surprisingly, the antiviral action is not related only to fighting oxidative stress, but also the infection/replication can be inhibited by the inventive dithiocarbamate compounds.

It could be shown that the inventive dithiocarbamate compounds induce genes, which act as antioxidant-induced transcription factors (Meyer et al., EMBO J., 12, 2005-2015, 1993). The heterodimeric transcription factor, AP1, can be induced by NAC and the inventive dithiocarbamate compounds, leading to DNA binding and transactivation. The activation of AP1 by the inventive dithiocarbamate compounds depends on protein synthesis and involves transcription of c-jun and c-fos genes. However, the activation of AP1, alone, is not responsible for the strong inventive inhibition of viruses.

Pyrrolidine dithiocarbamate (PDTC) is already known as a prooxidant and anti-oxidant, inhibitor of activation of the transcription factor NFκB, zinc ionophor, and metal-chelating agent. PDTC is described in Sherman et al., Biochem. Biophys. Res. Comm., 191 (3), 1301-1308, 1993, as an inhibitor of NFκB activation and of NO synthase. WO 01/00193 A2 concerns compositions comprising diethyldithiocarbamate in the picomolar and nanomolar range, which exhibit a strong action against apoptosis.

According to the invention, it could be shown that the inventive dithiocarbamate compounds exhibit strong action against RNA viruses which attack the respiratory tract and cause disease there—"respiratory RNA viruses"—both in vitro and in vivo.

According to the invention, the infection is counteracted already in a very early phase, even before extensive cell damage or even cell death occurs.

In the present invention, respiratory RNA viruses are taken to mean any viruses of humans and mammals that attack the body via the respiratory tract, i. e., the respiratory passages and lungs, and penetrate the body, triggering disease in the respiratory tract. Obviously, the biological processes that occur in this infection are so similar that the action of the inventive dithiocarbamate compounds occurs efficiently in analogous manner, in spite of the biological heterogeneity of this group of viruses. But, conversely, it has also been shown that action of the inventive dithiocarbamate compounds, alone, is not sufficient to successfully combat a virus infection caused by other viruses that get into the body through other routes of infection and pass through different biological cycles (e. g., which can be integrated into the host genome as a latent virus), or trigger disease in other organs, such as the brain.

In this respect, it has been shown, in the meantime, that treatment of AIDS patients with dithiocarbamates does not cause cure or improvement of the patients (Multicenter randomized placebo-controlled study of dithiocarb (Imuthiol) in asymptomatic and minimally symptomatic patients infected with human immunodeficiency virus (The HIV87 Study Group, AIDS Res. Hum. Retroviruses 1993, January; 9 (1), 83-89). Because of those results, no further clinical studies were done with latent viruses (see U.S. Pat. No. 5,686,436).

According to the present invention, the dithiocarbamate compounds, primarily, develop their particular activity in an early phase of the viral infection or if they are taken before the infection. Thus, the dithiocarbamate compounds according to the invention can prevent the outbreak of a virus infection if it they are taken prophylactically, for example, in places and at times at which there is a risk, or even an elevated risk, of respiratory virus infections, such as in regions with epidemics or in cold waves. The dithiocarbamate compounds according to the invention are preferably used to prevent virus infection.

The virus inhibition according to the invention is particularly preferred, but especially in the early phase of a respiratory virus infection that has already occurred. Then, the dithiocarbamate compounds according to the invention are used with the aim of inhibiting replication of the viruses, i. e., at a time before persistent damage has occurred in the infected individual. In that way, not only is it possible to prevent the consequences of progressive virus infection in the individual affected, but the spread of other infectious viruses to other individuals is also prevented; the danger of further infection is minimized, which is of great general effect and significance for health policy, especially with respect to human influenza virus.

The following viruses, in particular, are considered respiratory RNA viruses in the present invention: rhinoviruses, Coxsackie viruses, echoviruses, coronaviruses, enteroviruses, human orthomyxoviruses (such as influenza virus (A, B and C)), paramyxoviruses (such as parainfluenza virus and pneumovirus), respiratory syncytial virus (RSV) and other RNA viruses as long as they cause disease in (at least) the respiratory tract. Viruses or virus strains that do not cause disease in the respiratory tract but in another organ, such as the brain, e. g., meningitis virus, encephalomyocarditis virus, poliovirus, cardiovirus, etc., are not covered by the present application. Infection of epithelial cells of the upper or lower respiratory tract is common to the respiratory RNA viruses according to the invention. In addition, other organs can be attacked. The local inflammation that they cause in the respiratory tract is considered the principal cause of the typical symptoms of flu, such as runny nose, sore throat, hoarseness, coughing, vesicles, and, often, fever. The frequent occurrence of secondary infections in individuals with weakened immunity is also favored by infection with these respiratory viruses.

Within the scope of the present invention, picornaviruses are understood to be all the "true" picornaviruses, according to the current classification of the Picornaviridae based on King et al. ("Picornaviridae" in "Virus Taxonomy, Seventh Report of the International Committee for the Taxonomy of Viruses", (2000), Van Regenmortel et al., Editors; Academic Press 657-673), insofar as they attack the respiratory tract and cause disease there, i.e. the genera Enterovirus, Rhinovirus, Aphthovirus, Parechovirus, Erbovirus, Kobuvirus and Teschovirus. These viruses of the Picornaviridae family are characterized by similar genetic structure, protein composition, cultivation characteristics, and ability to resist heat or virucides.

It has been found that the present invention is particularly suitable for combatting the human-pathogenic and animal-pathogenic members of the true respiratory Picornaviridae, especially those of the genera Enterovirus (Enterovirus 70, 71, Cox sackie virus) and Rhinovirus (e. g., human Rhinovirus) and Aphthovirus (e. g., foot and mouth disease virus), whereas the advantages according to the invention could not be demonstrated for other viruses, including the picornaviruses that cause latent infections, such as HAV. This is probably also due to the fact that the group of "true" respiratory picornaviruses is so homogeneous, and that the pathophysiological processes which occur in the infections are so similar that the dithiocarbamate compounds according to the invention act analogously.

In the present application, "virus infection" is understood to be any attack of a respiratory virus on cells that includes, for example, one of the following steps: beginning with docking of the virus particle to a cell, and, in a later stage, introduction of the genetic information of the virus into the cell, as well as production of new virus particle parts and expression of infectious virus particles.

Furthermore, it is also possible to use oxidized forms of these compounds, especially dimers of them, because they are quickly metabolized to the reduced form in the organism, which is known per se. In the present application, "oxidized forms" are understood to be those compounds in which the S group is oxidized. Disulfiram is a preferred example of one such oxidized dimeric form, it is also known by the names "Antabuse" or "Abstinyl", and is a tetraethylthiuram disulfide ($C_{10}H_{20}N_2S_4$). Disulfiram is already known per se, and is used particularly for treatment of alcoholics. Disulfiram acts as a mediator in oxidoreductions and inactivates aldehyde dehydrogenase. When ethanol is taken, acetaldehyde accumulates in the body and exerts a pronounced negative effect on the general well being. Taking of Disulfiram and alcohol simultaneously results in anxiety states, nausea, loss of vision, chest pains, headaches, etc., these symptoms lasting from 3-4 days to as much as a week. For that reason, Disulfiram is administered therapeutically to alcoholics, since any subsequent consumption of alcohol should be avoided because of these severe negative effects.

Other known effects of Disulfiram are inhibitions of enzymes such as fructose-1,6-diphosphate dehydrogenase, xanthine oxidase, hexokinase, aldehyde oxidase and dopamine β-hydroxylase.

Disulfiram is also used to treat pediculosis and scabies, and to treat nickel dermatitis.

The metabolism of Disulfiram has already been studied in detail. See, for instance, Dollery, C., 1999, Therapeutic Drugs, Second Edition, Volume 1, Churchill Livingstone, Edinburgh. It is explained that the principal metabolite of Disulfiram in the body is diethyldithiocarbamate, and that the conversion proceeds very rapidly.

The oxidized forms of the dithiocarbamate compounds according to the invention are quite readily fat soluble, and can be provided, for instance, as agent for oral administration, the compounds being absorbed in the stomach. The compounds could also be used, in particular, as a powder spray. Further, the oxidized forms of the compounds according to the invention can be provided with hydroxyl groups to increase their water solubility so that they can made available as an aerosol. If the dithiocarbamate compounds according to the invention are provided in oxidized form, and especially the dimeric products, depot action of this agent is attained, i.e., the dithiocarbamate compounds according to the invention are gradually released to the body over a certain period and absorbed by the body. The oxidized dithiocarbamate compounds can also be implanted, as is known per se, in the body to be treated to attain this depot effect.

One preferred compound according to the invention is characterized in that $R_1$ and $R_2$, independently of each other, represent a $C_1$-$C_3$ alkyl or form an aliphatic ring with 4 to 6 C atoms along with the nitrogen atom. These have turned out to be particularly advantageous for treatment or prevention of a respiratory RNA virus infection.

It is preferable for the dithiocarbamate compound to be selected from pyrrolidine dithiocarbamate (PDTC) and N, N-diethyldithiocarbamate (DDTC). These compounds exhibit outstandingly strong activity against respiratory RNA virus infections.

An especially preferred virus infection is an infection with picornavirus, orthomyxovirus or paramyxovirus. The dithiocarbamate compounds according to the invention are particularly active against these virus infections.

Here, it is advantageous for the orthomyxovirus to be a human influenza virus, particularly selected from the group consisting of influenza A, influenza B, influenza C or for the paramyxovirus to be a parainfluenza virus or pneumovirus. The orthomyxovirus, preferably, is a mammalian influenza A virus and the picornavirus, preferably, is a rhinovirus, especially human or equine rhinovirus, an enterovirus, especially Enterovirus 70, 71, or Coxsackie virus, or an aphthovirus, especially foot and mouth disease virus or equine rhinitis virus A. As already explained above, those viruses or virus strains, which are included in the picornaviruses but which do not cause disease in the respiratory tract but rather in the brain or nerve cells, such as cardioviruses or polioviruses, are excepted. These virus infections are treated or prevented especially effectively with the compound according to the invention.

The Picornaviridae family includes a group of small RNA viruses, including the rhinoviruses (e. g., human rhinovirus), enteroviruses (e. g., Enterovirus 70, 71, Coxsackie virus, which is known, for instance, as a cause of hand, foot, and mouth disease), aphthoviruses (such as foot and mouth disease virus, which causes a disease in the mouth, as well as equine rhinitis virus A). With foot and mouth disease, for example, it is of particular interest to use the compound according to the invention to bridge the period between the vaccination and the time when the vaccine becomes effective (ca. 10-12 days), because the vaccinated animals are not protected during that period and, under some circumstances, will excrete large quantities of virus following infection without themselves being sick. Therefore, the compound according to the invention could be administered to the animals simultaneously with the vaccination and for perhaps about 2 weeks thereafter.

Orthomyxoviruses and paramyxoviruses are a subclass of the earlier collective designation for influenza viruses and other similar viruses. In humans, the paramyxoviruses cause measles, mumps, and respiratory and neurologic diseases. The paramyxoviruses include, among others, parainfluenza virus, mumps virus, Newcastle disease virus, respiratory syncytial virus (RSV), measles virus, and rinderpest virus. The influenza A, B and C viruses, which cause flu in humans, are members of the orthomyxoviruses.

The type A influenza viruses are responsible for most of the flu epidemics and all the pandemics. Influenza A viruses do occur in horses and pigs as well as in birds, such as the pathogens of the classical avian pseudoplague [Newcastle disease]; however, only the human influenza viruses and those of mammals, such as the horse, can be considered respiratory viruses in the true sense, as the biology of the avian influenza virus (AI) differs completely from that of the human influenza virus. Therefore, the AI virus cannot be considered a respiratory virus. In ducks, the virus replicates, primarily, in the intestinal tract; yet this is not the case in humans. As a result, AI viruses can also be isolated from feces of birds (Hinshaw et al., 1980, Canad. J. Microbiol.

26,622-9). In addition to that, the nucleotide variation rate of AI viruses is lower than those of the viruses that can be isolated from mammals. Evolution of the viral proteins in organisms other than birds, typically, exhibits rapid accumulation of mutations, which do not occur in the AI viruses (Gorman et al., 1991, J. Virol. 65: 3704-14; Ludwig et al., 1995, Virology 212: 555-61). The receptor specificity varies among different influenza viruses. Most of the AI viruses preferably bind to the alpha-2-3-galactose-sialic acid receptor. In contrast, human influenza viruses bind primarily to the alpha-2-6-galactose-sialic acid receptor (Rogers and Paulson, 1983, Virology 127, 361-73; Baum and Paulson, 1990, Acta Histochem., Suppl. 40: 35-8).

As the viruses covered by the invention cause many widespread diseases in humans and mammals, the antiviral action of the dithiocarbamate compounds according to the invention is particularly important with respect to those viruses. As the dithiocarbamate compounds according to the invention are outstandingly active against those viruses, the inventive dithiocarbamate compounds are particularly suitable for production of a series of agents to treat or prevent those virus infections. The dithiocarbamate compounds according to the invention can be produced easily and cost-effectively in large quantities, and they are scarcely toxic to the cells being treated, even at high concentrations.

In one advantageous embodiment, the dithiocarbamate compounds according to the invention are provided in the agent at a concentration of from 0.01 to 5000 mM, preferably, 1 to 300 mM, and, especially preferably, 10 to 100 mM. The dithiocarbamate compounds according to the invention are particularly active against respiratory RNA virus infections at these concentrations and exhibit few or no side effects. The concentration to be used is selected according to the virus infection to be treated, depending on the intensity of the virus infection, or according to the organism to be treated, whether animal or human, and depending on the age.

It is particularly suitable to provide the dithiocarbamate compounds according to the invention at a concentration of from 10 mM to 1 M. In this case, the dithiocarbamate compounds according to the invention are present in highly concentrated form, and the agent can be diluted before treatment, depending on the concentration desired.

The agent preferably further comprises a pharmaceutically acceptable carrier. Any of the pharmaceutically acceptable carriers known to those skilled in the art of pharmacy can be used, such as phosphate-buffered saline solution (PBS) or sodium chloride solutions with different buffers, or formulations containing liposomes, in which case, again, the carrier is selected depending on the type of treatment, the virus infection, and the organism being treated.

The agent is preferably one that is administered orally, intranasally, intravenously, parenterally, rectally, as eye or ear drops, a gargle, or an aerosol. The mode of administration especially depends on the virus infection being treated. For example, an infection in the respiratory tract is treated with an agent to be administered intranasally, such as in the form of an aerosol comprising the dithiocarbamate compounds, because the virus infection is treated right at the site of the virus attack. Depending on the mode of administration, the dithiocarbamate compounds are provided at a particular concentration, or the agent includes additional substances favorable for that form of administration. It is obviously possible to provide the agent in a dried form, in which case it is diluted with a suitable solvent before the treatment.

One particularly advantageous use is if the agent comprises further antiviral substances. In this way, the virus infection in the respiratory tract can be attacked from several sides, or a whole range of different viruses can be weakened or completely eliminated at the same time. Such further antiviral substances include substances inhibiting replication, immune-stimulating substances, neutralizing antibodies, etc. as well as optionally substances that can support the immune system generally.

Preferably, the agent comprises a combination of at least two different dithiocarbamates according to the invention, particularly a mixture of PDTC and DDTC. The dithiocarbamate compounds according to the invention exert pro-oxidative and anti-oxidative functions in cells. Their anti-oxidative action includes elimination of hydrogen peroxide, removal of superoxide radicals, peroxynitrites, hydroxyl radicals, and lipid peroxidation products. By these eliminations, the dithiocarbamates are oxidized to thiuram disulfides. Thiuram disulfides are responsible for the pro-oxidative actions of dithiocarbamates, and, in many cases, the formation of thiurams depends on the presence of metals. It has been reported that, perhaps, the anti-apoptotic activities of dithiocarbamates are related to inactivation of caspases by thiol oxidation.

It is particularly preferred for the agent according to the invention to further comprise substances selected from antibiotics, vaccines, immune-suppressants, stabilizers, immune-stimulating substances, blood products, or mixtures thereof. If additional antibiotics are used, bacterial infections can be combatted along with the respiratory viruses. If the agent comprises additional vaccines, understood here to mean both passive and active vaccines, certain other, further virus infections that can easily infect the weakened organism are prevented at the same time as the inventive treatment or prevention of the virus infection. In addition, stabilizers can also be added to increase the storage stability or lifetime. Blood products, for example, are plasma, blood corpuscles, clotting factors, etc., depending on the treatment to which the patient is subjected.

It is suitable to use the agent to inhibit virus propagation. In that manner it is ensured that an existing infection does not spread, but, in contrast, is treated very quickly.

According to a further aspect of the present invention, the invention also concerns a disinfectant comprising at least one inventive dithiocarbamate compound as described above. In this invention, "disinfectant" means any substance used outside a human or animal organism to combat viruses, as on surfaces, in agents, especially in media, or for cell cultures. In particular, such disinfectants can be used if the substance to be treated is sensitive to other more aggressive antiviral substances. For instance, disinfectants comprising the inventive dithiocarbamate compounds are suitable as additives to media or for treating cells or cell cultures which react sensitively to other more aggressive disinfectants or antiviral substances. The dithiocarbamate compounds according to the invention have shown themselves to be particularly effective in treatment or prevention of respiratory RNA virus infections of respiratory cells and cell cultures.

The disinfectant is particularly effective if it comprises the dithiocarbamate compounds according to the invention at a concentration of from 10 μm to 5 M, in particular 30 μm to 1 M. These concentrations, on one hand, are active against respiratory RNA virus infections and, on the other hand, such a disinfectant is outstandingly gentle, for example, if it is used as an antiviral substance for cell cultures. Here, the concentration depends on the nature or on the advanced stage of the virus infection, and on the substance used for treatment, for instance, on the nature and sensitivity of the cells. Obviously, it is also possible to provide the disinfectant as a concentrate, in which case it is diluted before use to the desired concentration of the dithiocarbamate compounds according to the invention, using a suitable solvent.

The disinfectant preferably comprises further disinfecting, in particular antiviral, substances. These substances, known to anyone skilled in the art in the field of microbiology, are added particularly if other viruses are to be combatted at the same time, such as DNA viruses. Obviously, furthermore antibacterial substances, especially antibiotics, can also be added.

A further aspect of the present invention concerns a process for disinfecting surfaces, media or cell cultures, wherein a disinfectant according to the invention, such as is described above, is applied to the surface or cell culture, or is added to the medium, respectively. To disinfect a surface, for instance, it is sufficient to clean the surface with the disinfectant. In the case of media and cell cultures, the disinfectant can exert its action over longer periods, and the concentration of the disinfectant can be varied as described above, depending on the respective purpose.

According to another aspect of the present invention, the invention concerns treatment or prevention of a respiratory RNA virus infection with the inventive dithiocarbamate compounds. Here, an agent comprising the inventive dithiocarbamate compounds as described above is administered, in a suitable form and at a suitable concentration, to the patient or animal.

The present invention will now be explained in more detail by means of the accompanying examples and figures, but it is not limited to them.

EXAMPLES

Example 1

Reduction of Production of Infectious Rhinovirus Particles by PDTC

Figure 1:
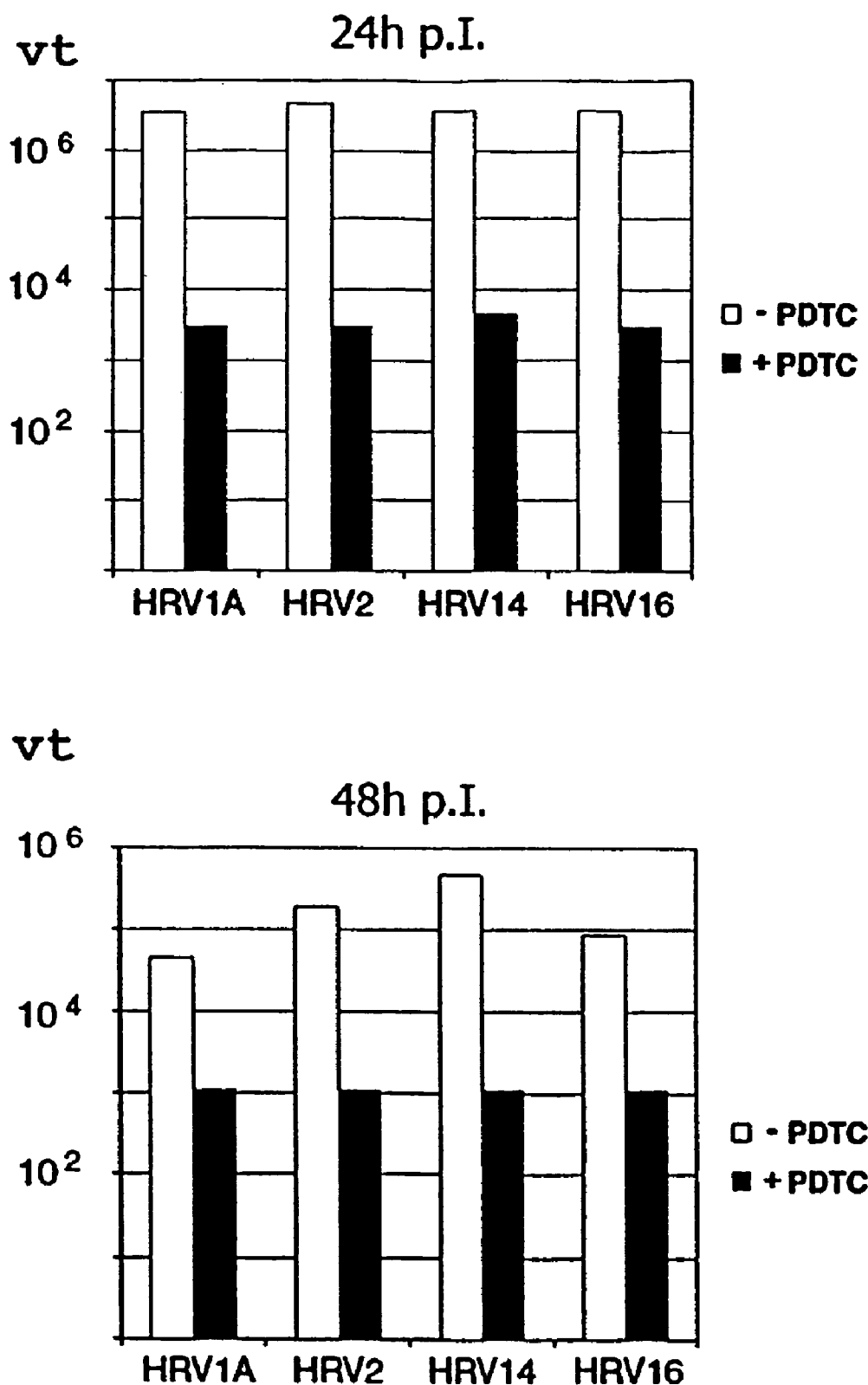
FIG. 1 is a graphical representation showing the inhibitory action of PDTC on HRV replication in cell cultures.

PDTC was added after infection of cells with various HRV serotypes to test the effectiveness during infections by HRV. HeLa cells were infected with HRV serotypes 1A, 2, 14 and 16 with 20 $TCID_{50}$ (tissue culture infectious dose 50) per cell. PDTC was added at the same time to a concentration of 125 μm in the medium. Excess virus was removed 4 hours after infection, while PDTC was added to the fresh medium. 24 hours (FIG. 1, top) and 48 hours (FIG. 1, bottom) after the infection (p. I.), the supernatants were collected and the amount of virus progeny was determined by $TCID_{50}$ tests. Treatment of cells with PDTC reduced the virus titer (vt) by $10^3$ after 24 hours (FIG. 1, top). The supernatants collected from PDTC-treated cells 48 hours after infection also showed a significant reduction of the virus titer (FIG. 1, bottom). These tests show that PDTC has strong anti-viral action against various HRV serotypes.

Example 2

Figure 2:
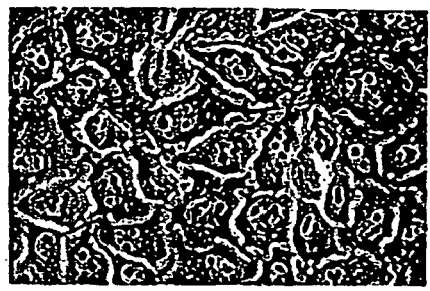
FIG. 2 shows the inhibition by PDTC of cytopathic effects induced by rhinoviruses.
Figure 2:
Figure 2:
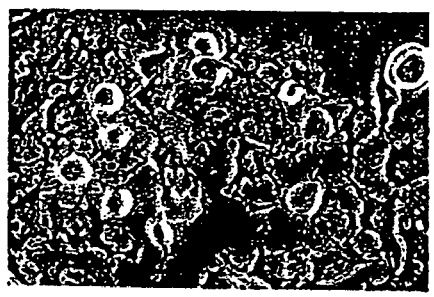
Figure 2:

PDTC Inhibits HRV-induced Cytopathic Effects and Increases the Viability of Infected Cells Morphological changes in the cells, called "cytopathic effects" (CPE) occur in the late stages of a rhinoviral infection. These HRV induced CPE are characterized as cell rounding, shrinkage, deformation of the nucleus and chromatin condensation. When HeLa cells are infected with HRV2, HRV14, HRV1A and HRV16 at 100 $TCID_{50}$ per cell, a distinct cytopathic effect is visible after 8 hours post-infection. Addition of PDTC during the infection prevents the appearance of these cytopathic effects. FIG. 2 shows that the morphology of cells infected in the presence of 125 μM PDTC (see the lower right figure) cannot be distinguished from the morphology of non-infected (n. i.) cells 8 hours after the infection (see the two upper figures).

Thus, the PDTC treatment attacks the virus infection at a very early stage, so that more extensive cell damage is prevented.

Example 3

Increase of Viability of Infected Cells by PDTC and DDTC

A cell proliferation assay was done to test the effect of PDTC or DDTC on the viability of the cells during a viral infection.

A Cell Titer 96® $Aq_{ueous}$ Non-radioactive Cell Proliferation Assay (Promega; Madison, Wis., U.S.A.) was done according to the manufacturers instructions. Cells were placed in 96 well plates one day before the infection. These cells were infected with various HRV serotypes at 20 $TCID_{50}$/cell. The viability of the cells was determined by addition of a tetrazolium substance, incubation for 2 hours at 37° C., and measurement of the absorption at 492 nm.

Figure 3A:
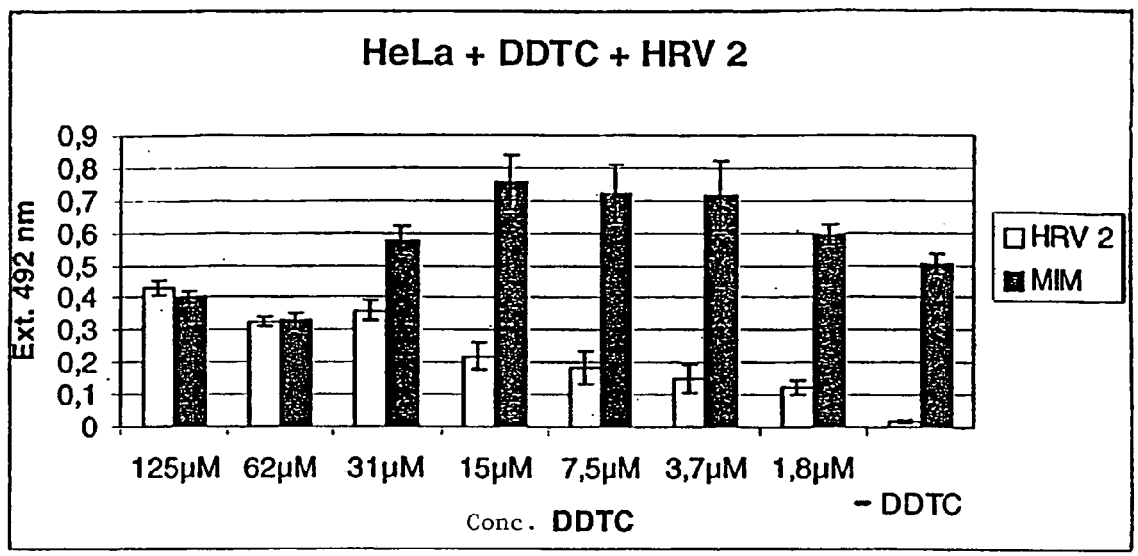
FIG. 3 shows the increase of cell viability due to PDTC and DDTC.
Figure 3B:
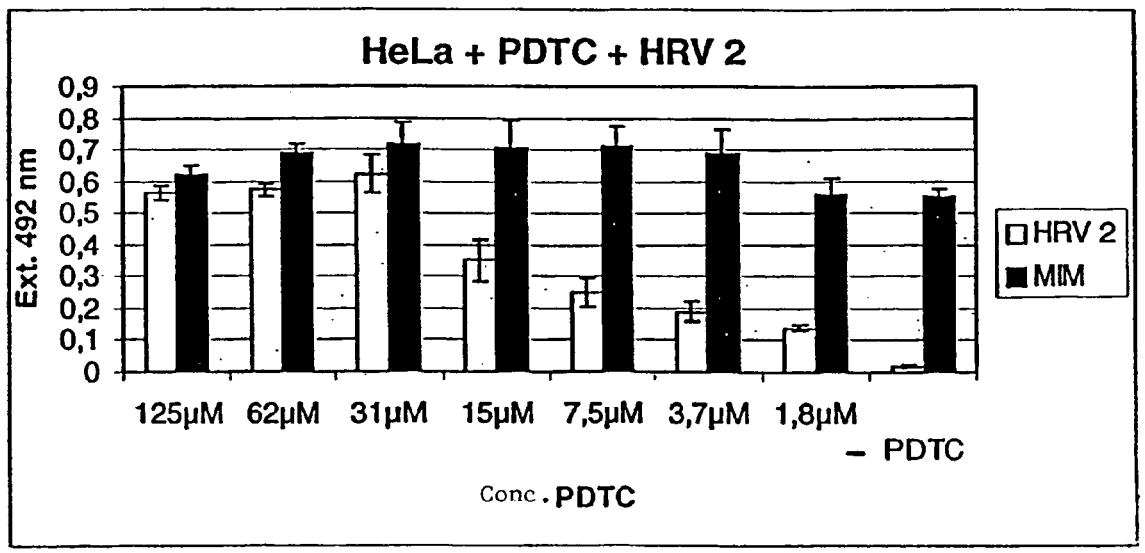

Twenty-four hours after infection with HRV2, HeLa cells showed complete loss of their metabolic activity, compared with noninfected HeLa cells (mock infection medium=MIM). It can be seen in FIG. 3 (Top: DDTC; bottom: PDTC) that the viability of the cells is significantly increased by adding even slight concentrations of PDTC or DDTC. PDTC or DDTC alone has only minor effects on uninfected cells. The concentration used to inhibit the viral infections exhibits no toxicity, though ("-" means "without").

Example 4

Dependence of the Efficacy of PDTC on the Time [of Administration]

Figure 4A:
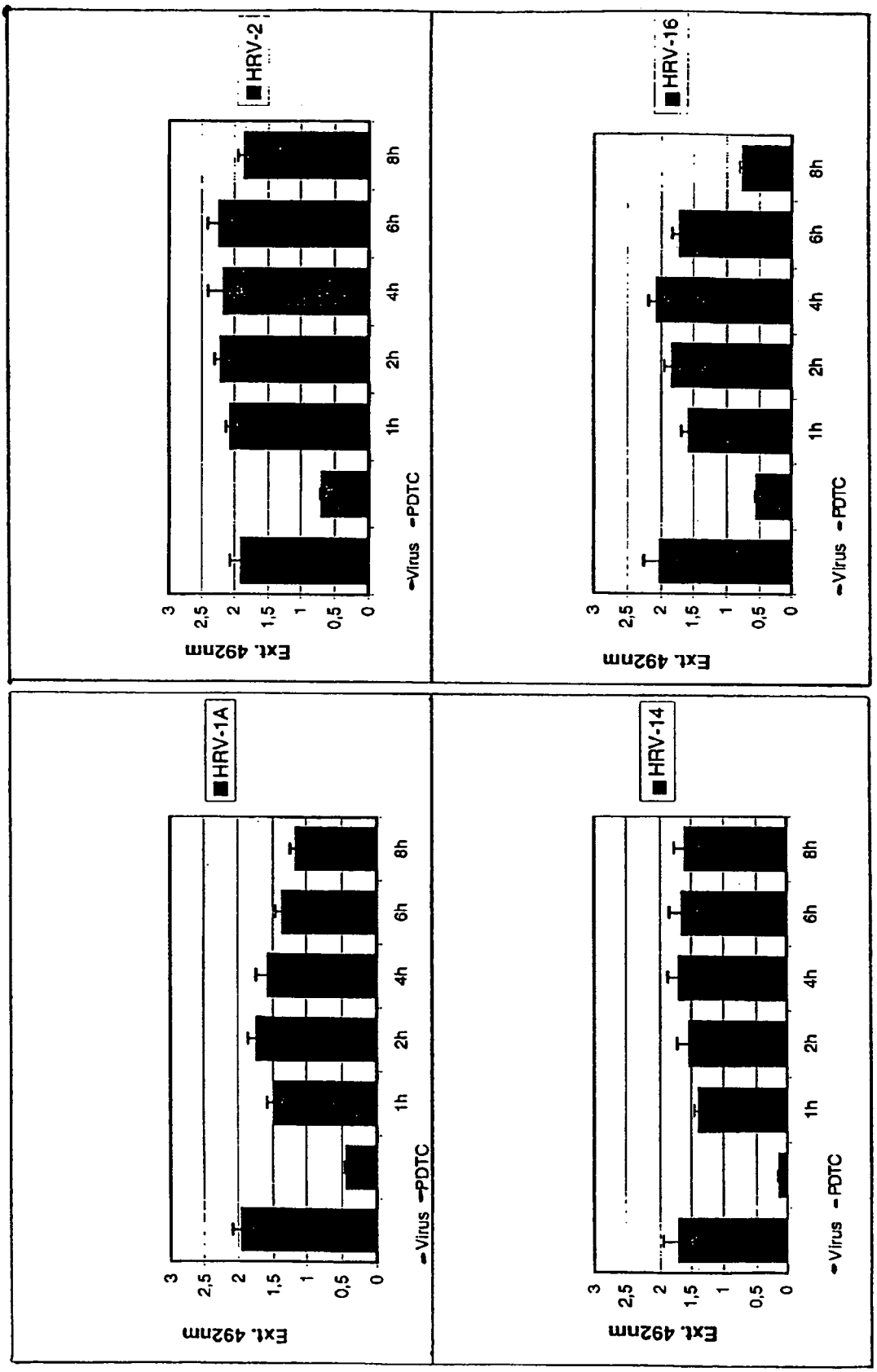
FIG. 4 shows the effect of a PDTC treatment with regard to its dependence on the time.

To determine the stage of the viral life cycle attacked by PDTC, PDTC was added at various times following virus infection with 20 $TCID_{50}$ per cell, and proliferation assays were done. It was shown that addition of PDTC (125 µM) within the first six hours after infection ("-" means "without") offers the best protection against virus induced loss of proliferation (FIG. 4A). This effect is also not specific for a single serotype, as HRC serotypes 1A, 2, 14 and 16 were used. Only PDTC treatment (125 µM) of the cells more than 8 hours after infection reduced the protective effect.

Figure 4B:
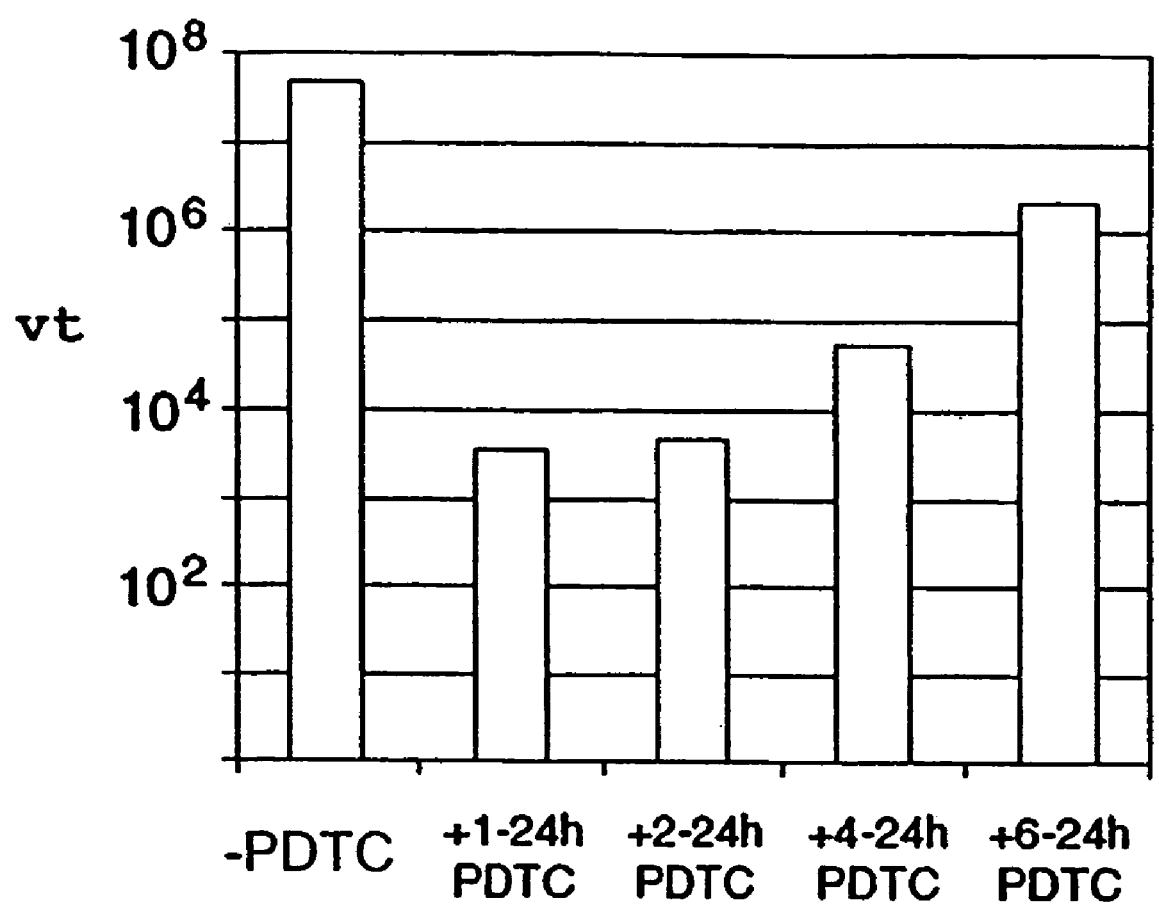

Similar results were obtained if the viral titers (vt) were determined in the supernatants of infected and PDTC-treated cells (see FIG. 4B). Addition of PDTC up to four hours after infection reduced the titer of the HRV2 produced by $10^3$. Even if the PDTC treatment was started only 6 hours after infection, the viral titers produced were significantly reduced. These results show that addition of PDTC has an antiviral effect even when it is done at later stages during the infection, and that the viability of the cells is increased while the amount of infectious viruses is dramatically reduced.

This shows that the antiviral action does not occur just in the early stages of the viral life cycle, such as during receptor binding or entry into the cell.

Example 5

Investigation of the Course of HRV Infection in the Presence of PDTC

Various proteolytic activities were determined to examine the course of a rhinoviral infection in the presence and absence of PDTC. Enzymatic splitting of the cellular translation initiation factors 4GI (eIF4GI) and 4GII by viral 2A protease, ending host cell protein synthesis, is one characteristic proteolytic activity that occurs in the course of infection with rhinoviruses and enteroviruses. Depending on the HRV serotype, eIF4G proteins are split in an early stage of infection. Another splitting activity during a rhinoviral infection, only recently described, is splitting of the intermediary filament protein cytokeratin 8. This splitting also depends on the 2A protease, but occurs at a later stage of the infection. In order to investigate the effect of a PDTC treatment on the course of a virus infection, a Western blot analysis was done to analyze these 2A protease substrates.

Medium was removed at the indicated times for the Western blot analysis. The cells were lysed by adding 100 µl of protein buffer (8% sodium dodecyl sulfate, 20% β-mercapto-ethanol, 20% glycerol, 0.04% bromphenol blue). 20 µl protein extract was separated by SDS-PAGE on each track, and blotted onto PVDF membranes. The incubation with antibodies was done with 0.1% Tween 20 and 5% skim milk powder in TBS. Polyclonal rabbit antibodies to eIF4GI were used for the immunodetection. Anti-rabbit immunoglobulins conjugated with alkaline phosphatase were used as the secondary antibodies. Staining was done with the alkaline phosphatase reaction. The molecular weights were determined by using a prestained SDS-7B marker (Sigma).

Figure 5:
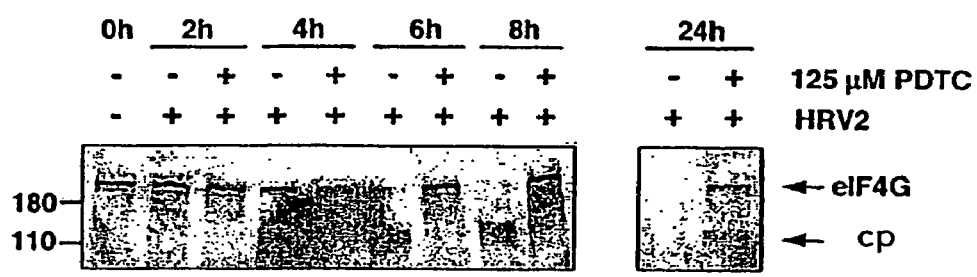
FIG. 5 shows the splitting of eIF4GI.

Splitting of eIF4GI can be detected 4 hours after infection in HeLa cells infected with HRV2 (100 $TCID_{50}$ per cell). (cp stands for splitting product, "cleavage product"). Splitting is complete 8 hours after infection (FIG. 5). No splitting of eIF4GI can be detected at those times in infected cells in the presence of PDTC. At later times, about 24 hours after infection, slight eIF4GI splitting can be detected even in cells treated with PDTC.

This shows that either the protease function is blocked, or that the amount of viral proteins is greatly reduced.

Example 6

Detection of Viral Envelope Proteins

Figure 6:
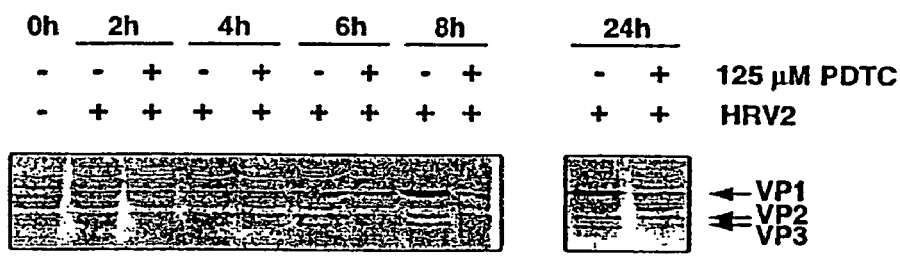
FIG. 6 shows a Western Blot analysis for determination of expression of rhinovirus capsid proteins.
Figure 7A:
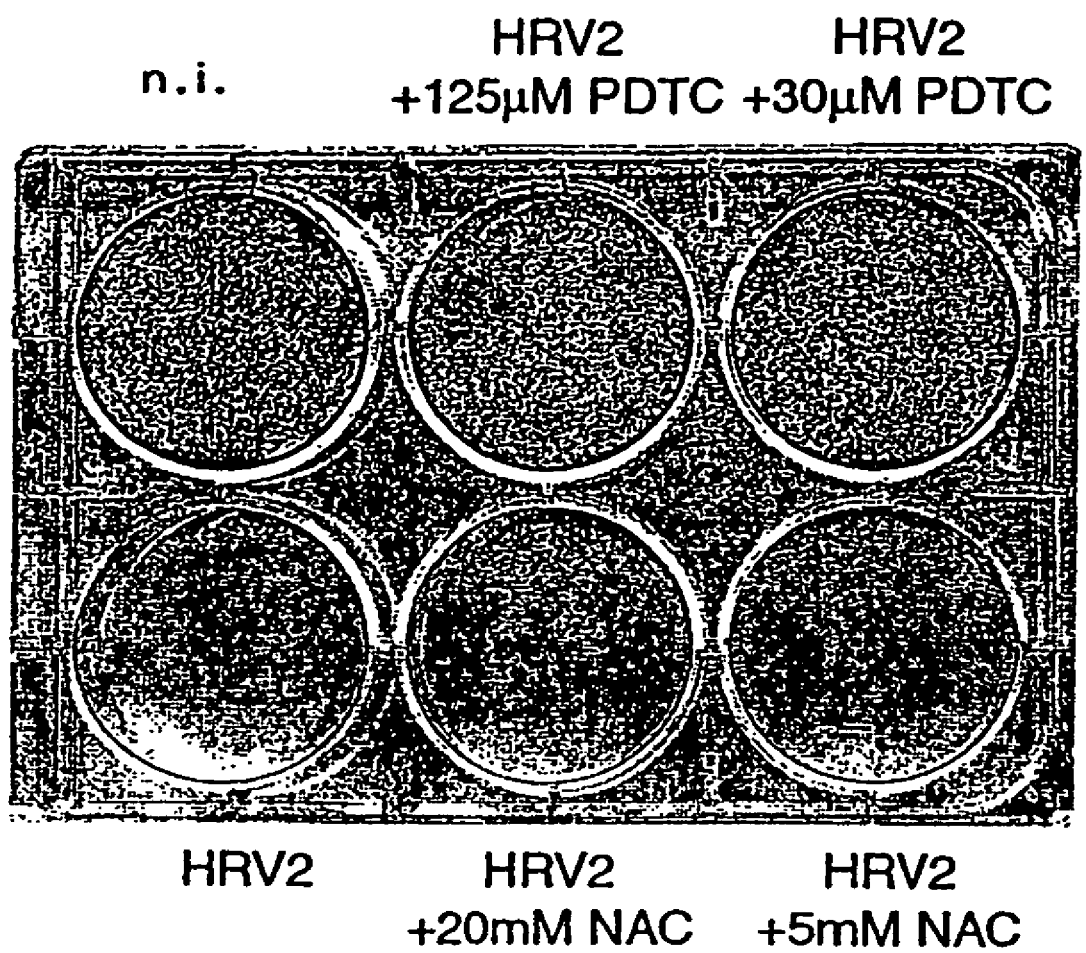
FIG. 7 shows the effect of other antioxidants on the HRV infection.
Figure 7B:
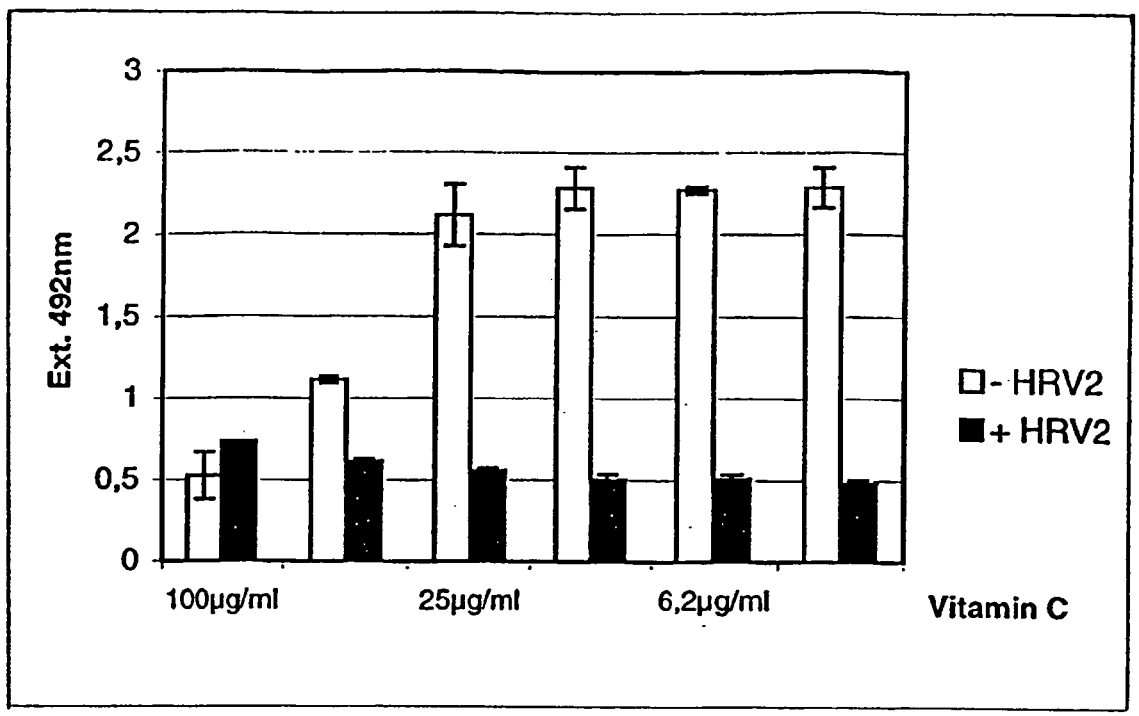
Figure 7C:
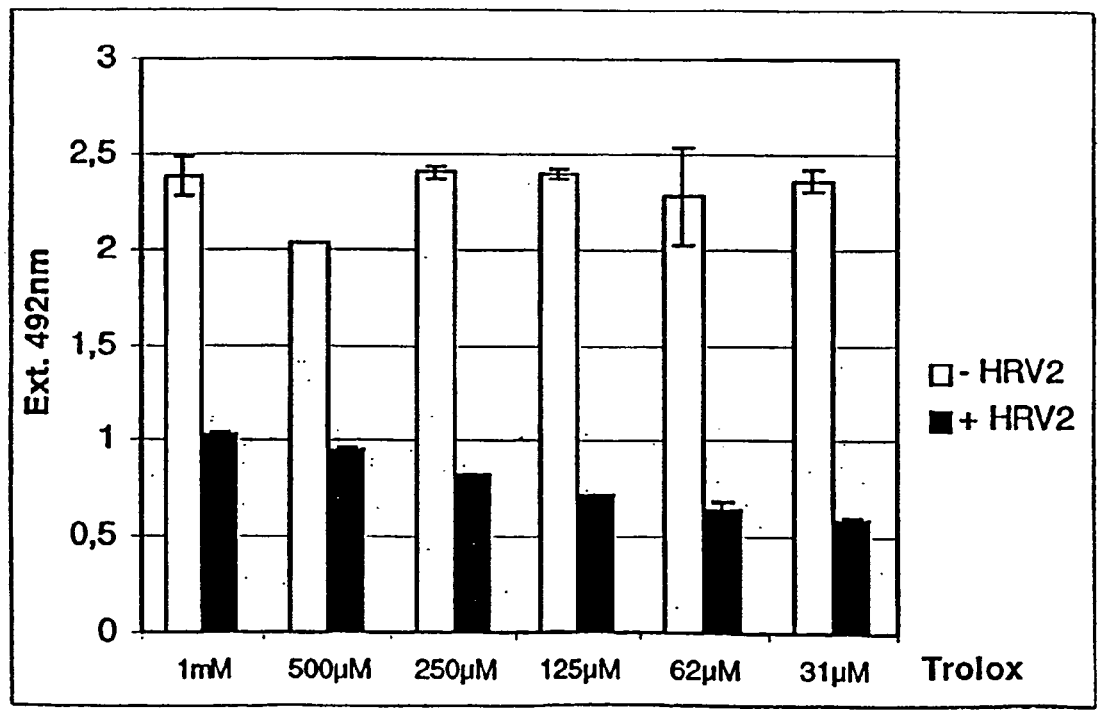
Figure 7D:
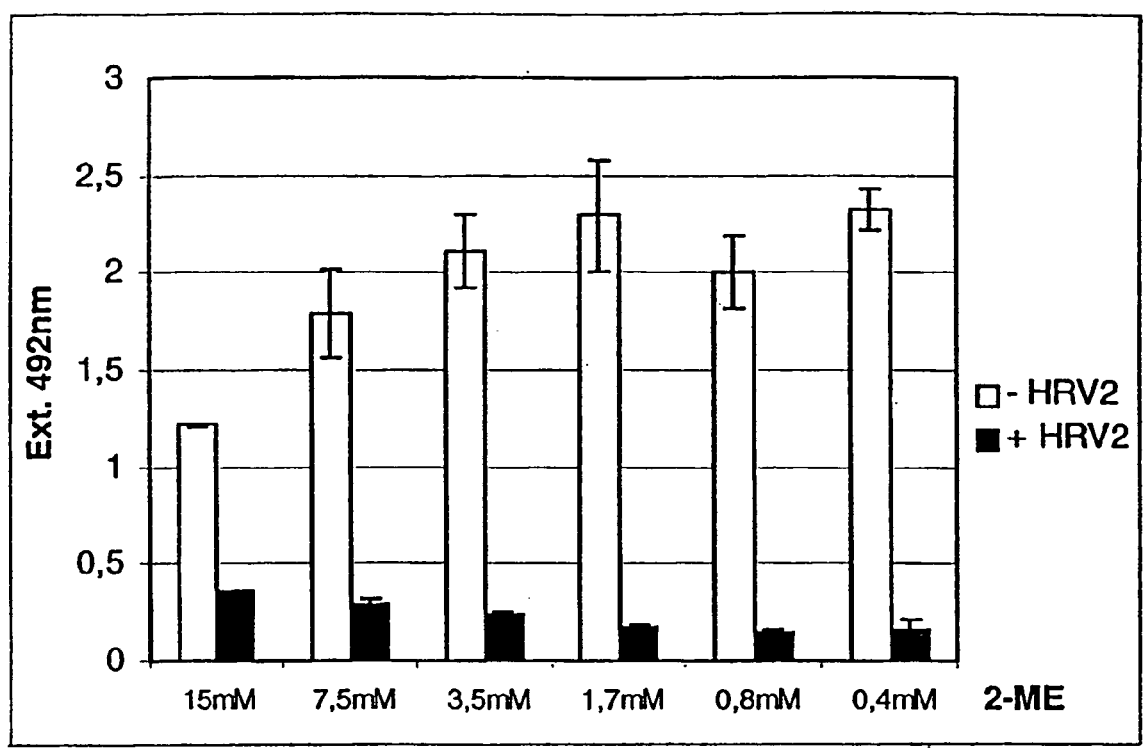

To determine the effect of PDTC on the expression of viral proteins, capsid proteins of HRV2 were detected by Western blot analysis in protein extracts from HRV2-infected HeLa cells (100 $TCID_{50}$ per cell) (see FIG. 6). The Western blot analysis was done as described above in Example 5, with use of a polyclonal rabbit antiserum against HRV2. Significant amounts of the rhinoviral proteins VP1, VP2 and VP3 were detected in untreated cells six hours after infection. A PDTC treatment prevented expression of those capsid proteins within the first 8 hours after infection. Weak expression of VP1, VP2 and VP3 was detected only at a later time, about 24 hours after infection.

This shows that PDTC delays production of viral proteins, explaining the anti-rhinoviral action of PDTC as well as its protective action on cells.

Example 7

Determination of the Dependence of the Antiviral Action on the Redox Potential

Other antioxidants were tested for their inhibitory action during a HRV2 infection of HeLa cells (FIG. 7). HeLa cells were infected with HRV2 (100 $TCID_{50}$ per cell) in a 6 well plate ("n. i." means "not infected"). The medium was removed 1 hour after the infection, and fresh medium, or media with various concentrations of PDTC or NAC, was added. After 24 hours, the cell lawn was washed with PBS and stained with crystal violet. It is apparent in FIG. 7A that the infection with HRV2 destroys the cell lawn. PDTC, but not NAC, can prevent that effect. The efficacies of Vitamin C, Trolox, and β-mercaptoethanol (2-ME) were determined as described in Example 3 (FIGS. 7B, C, D). It was shown, surprisingly, that none of these antioxidants had any protective effect during viral proliferation. The toxic effects of the substances in the absence of virus were tested as controls. A high dose of Vitamin C (100 µg/ml) severely inhibits cell growth.

This shows that the antiviral action of PDTC is not due to its antioxidative action, but is apparently related to other properties.

Example 8

Figure 8:
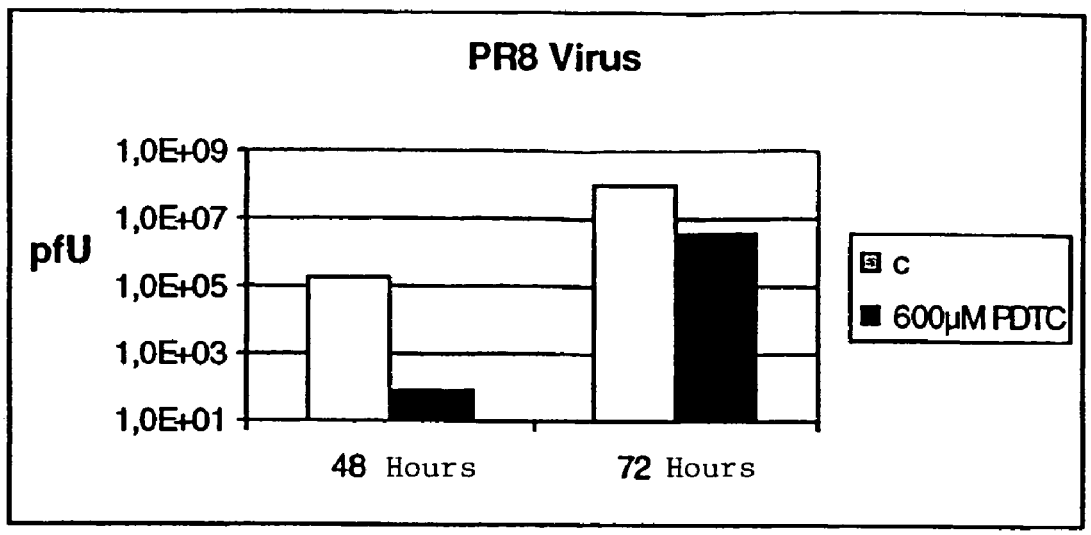
FIGS. 8 and 9 show the effect of PDTC on influenza virus replication.

Action of PDTC on Influenza Virus Replication $5 \times 10^5$ vero cells were infected with influenza virus A/PR8/34 or Vienna/47/96, with an m. o. i. (multiplicity of infection) of 0.01 and incubated for 1 hour at room temperature. Then, the inoculum was removed and infection medium containing 5 µg/ml trypsin and 600 µM PDTC were added. The supernatants were removed after 48 and 72 hours, and the virus titers in the supernatants were determined by a standard plate assay. As shown in FIG. 8, the virus titer from A/PR8/34 was reduced by more than 2 log steps, compared with the control sample (c).

Figure 9:
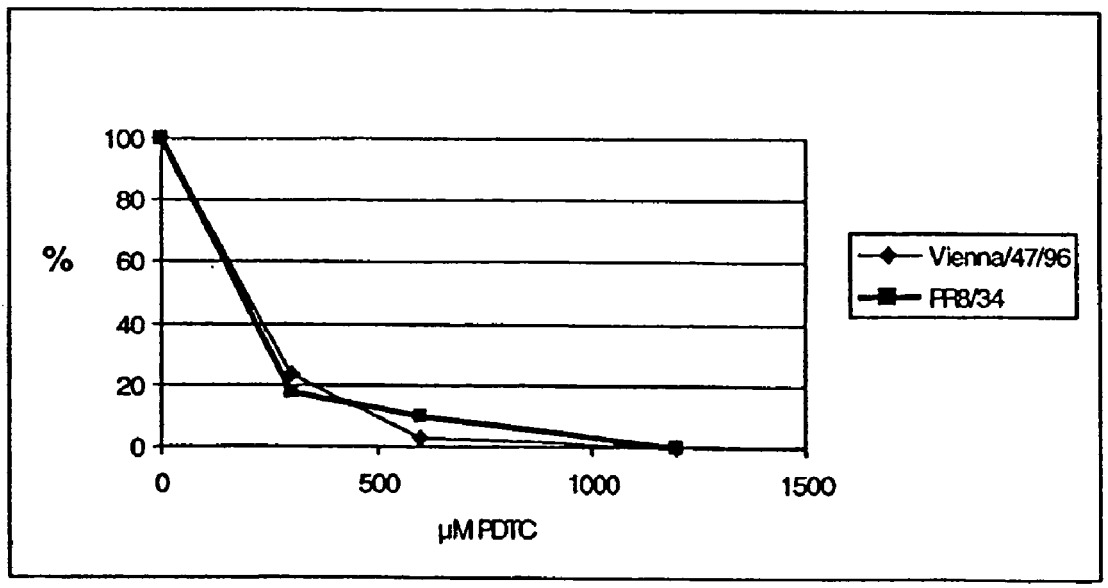

To test the efficacy of the PDTC, a $TCID_{50}$ (50% tissue-culture-infective dose) assay was done with and without PDTC. $TCID_{50}$ was calculated at each concentration by the method of Kaerber: 96 well microtiter plates were infected with two-fold dilutions of the specified virus. One hour after the infection, the supernatant was removed and media containing the specified concentrations were added. The numbers of infected cells were determined after 4 days. FIG. 9 shows that the $TCID_{50}$ was reduced by 76.4% and 82.2%, respectively, for A/PR8/34 and A/Vienna/47/96 at a PDTC concentration of 300 µM. More than 99.9% inhibition was attained for both viruses at a concentration of 1200 µM.

Example 9

Determination of the Effective Concentration of PDTC

Figure 10:
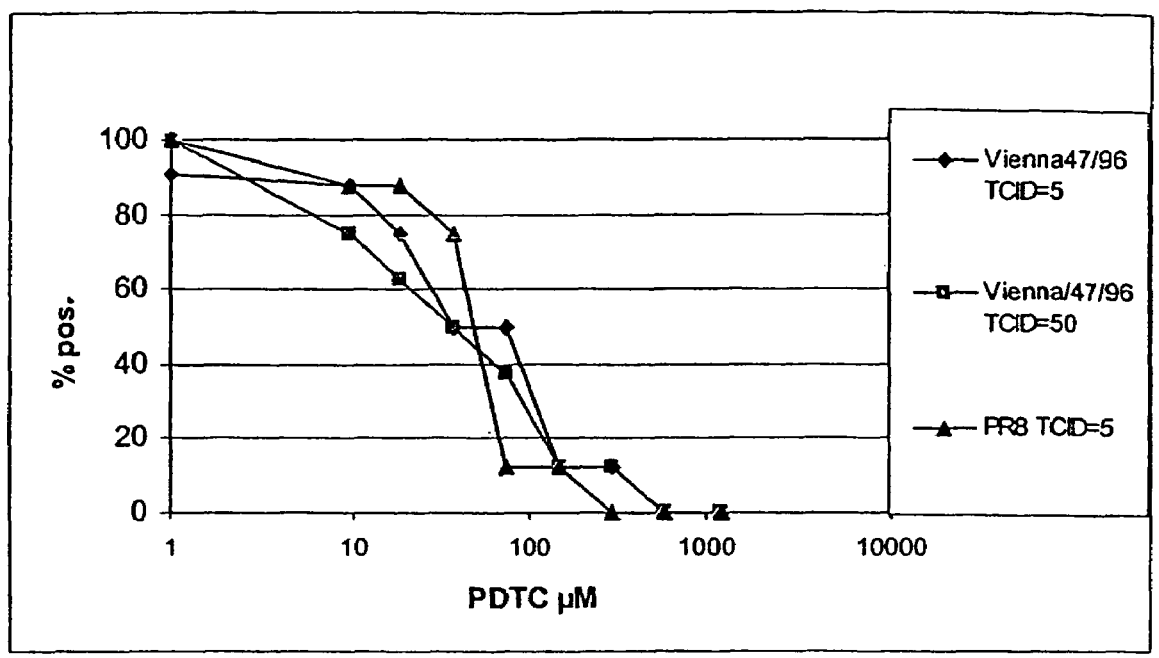
FIG. 10 shows the concentration dependence of the action of PDTC on vero cells infected with influenza virus.

The effective concentration of PDTC was determined using a CPE (cytopathic effect) reduction assay. Vero cells were cultivated in 96 well microtiter plates and infected with 5 $TCID_{50}$ per well and 50 $TCID_{50}$ per well of influenza A/PR8/34 and with 5 $TCID_{50}$ per well of influenza A/Vienna/47/96. The supernatants were removed 1 hour after infection, and medium with 5 µg/ml trypsin and a 2-fold dilution series of PDTC beginning at a concentration of 1200 µM was added. The plates at each concentration were examined visually for cytopathic effects with respect to the control sample over the following 4 days. The occurrence of cytopathic effects with respect to the control sample was calculated for each concentration. 100% positive means complete lysis in all wells. It can be seen in FIG. 10 that 50% reduction of positive wells was attained at PDTC concentrations between 50 and 100 µM. Complete inhibition of cytopathic effects was attained at a PDTC concentration of 600 µM for all viruses.

Example 10

Determination of the PDTC Action In Vivo

Figure 11A:
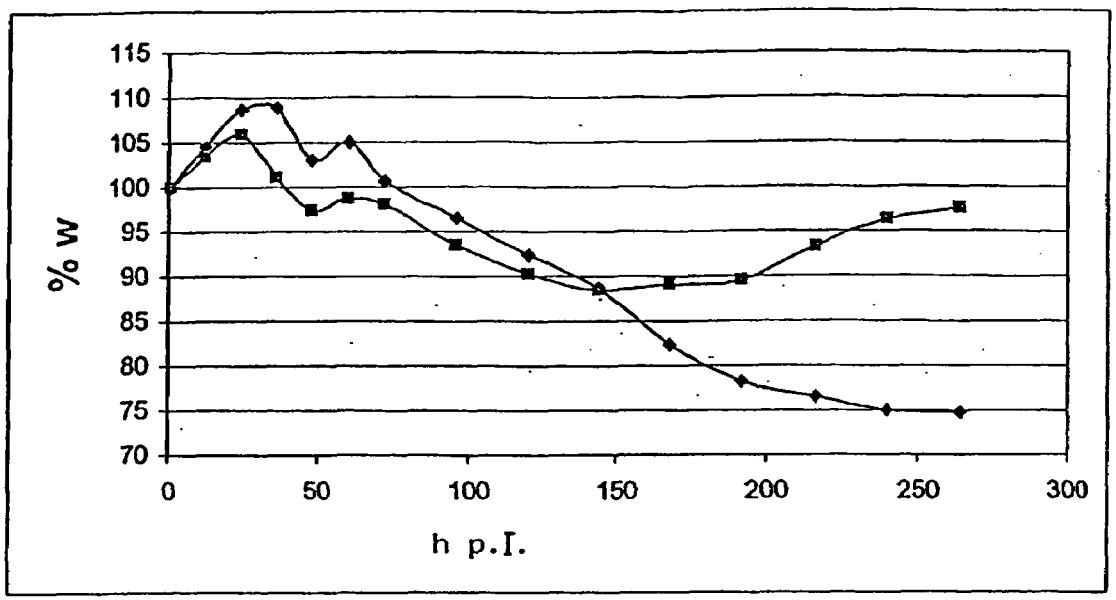
FIGS. 11A and 11B show the effect of PDTC on mice infected with influenza virus.
Figure 11B:
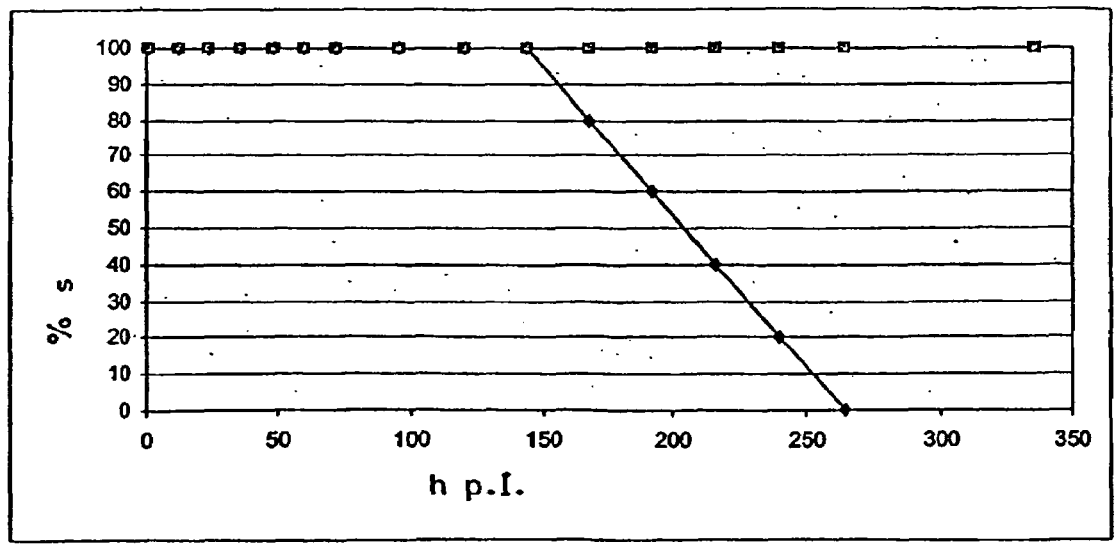

Ten C57/BL6 mice were inoculated intranasally with a lethal dose (50 µl $10^7$ pfU). One hour later, they were treated intranasally with 25 µl 600 mM PDTC or with 25 µl PBS. The mice were examined and treated every 12 hours for the first 48 hours and then every 24 hours. The weights of the mice were determined and reported in % of the initial weight (% w) (FIG. 11A). FIG. 11B shows that all the mice treated with PDTC (squares) survived the virus infection and gained weight 7 days after the infection. All the mice treated with PBS (diamonds) died within 12 days after the infection (% s=% surviving).

This shows that PDTC alone exhibits strong activity against influenza virus infections in vitro and in vitro.

Example 11

Antiviral Activity of PDTC Against Equine Rhinitis A Virus (ERAV)

The reduction of ERAV viral propagation by addition of PDTC was investigated as follows: vero cells were infected with 10 $TCID_{50}$ ERAV per cell. At the same time, PDTC was added at different concentrations (1 mM-50 µM). The inoculum was removed 4 hours after infection, and fresh medium with PDTC was added. The supernatants were removed 24 hours after the infection, and the viral titers were determined in a standard plate assay.

Figure 12:
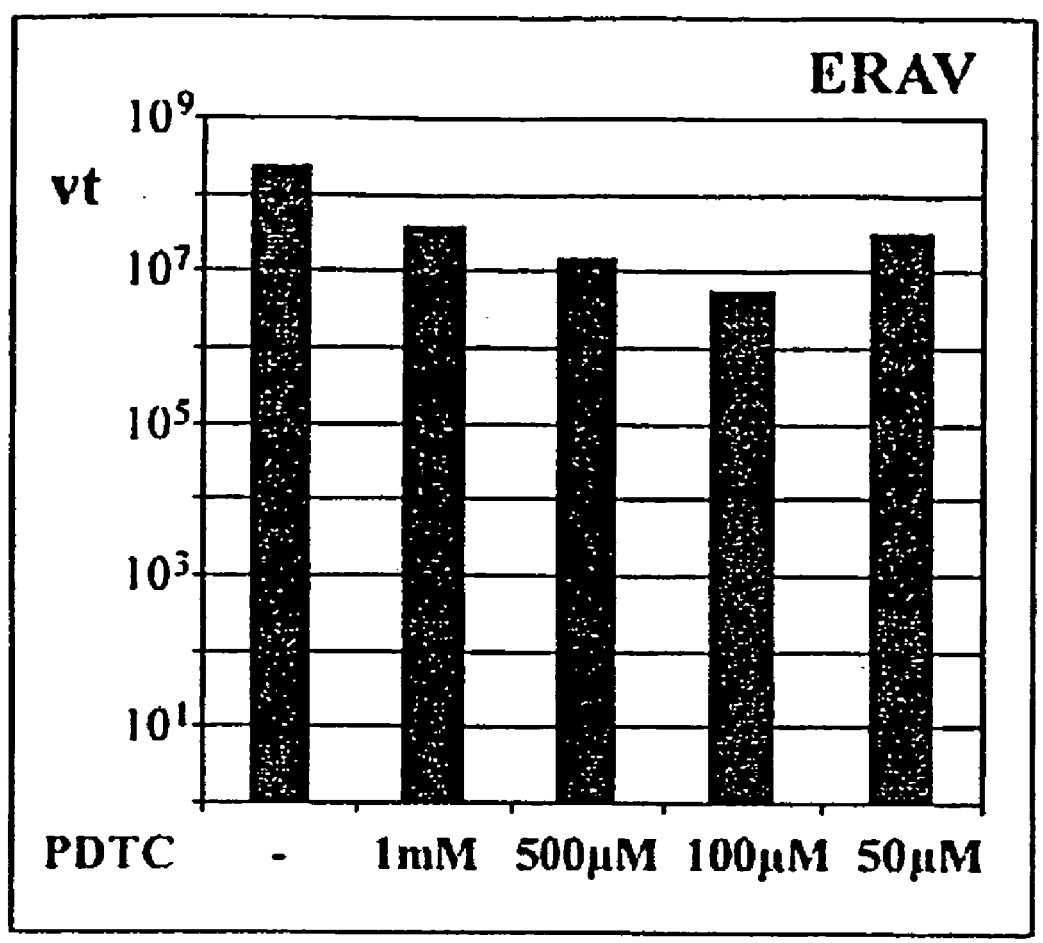
FIG. 12 shows the effectiveness of PDTC against ERAV.

FIG. 12 shows that the virus titer (vt) in the supernatant decreases in comparison to untreated cells (-).

Example 12

Effect of PDTC on Proliferation of Foot and Mouth Disease Virus (FMV) in Cell Culture The concentration of PDTC effective against cell destruction caused by FMV virus was determined by a CPE (cytopathic effect) reduction assay.

IB-RS-2 cells were cultivated in 96 well microtiter plates, infected with 0.1 $TCID_{50}$ per cell of FMV virus O-Manisa and incubated for 1 hour at 37° C. Then, the inoculum was removed and infection medium with the specified concentrations of PDTC (10 µM to 1200 µM) was added. The number of infected wells was determined after 24 hours by microscopic observation of the cytopathic effect.

Figure 13A:
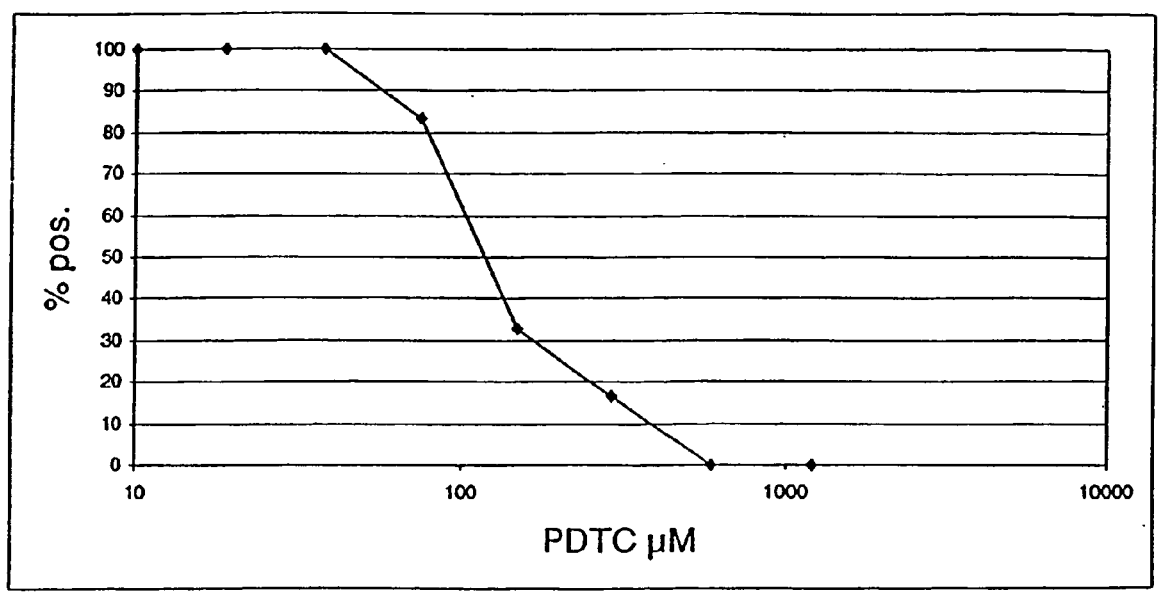
FIGS. 13A and 13B show the effectiveness of PDTC against FMV.

FIG. 13A shows that the number of infected wells (% pos.) after 24 hours depends on the PDTC concentration. 600 µM PDTC gives the cells 100% protection against the cytopathic effect of the virus. A 50% reduction of infected wells was attained in the concentration range of 75 µM to 150 µM.

To test the action of PDTC on FMV virus replication, IB-RS-2 cells in T25 $cm^2$ cell culture bottles were infected with FMV virus O-Manisa at 0.001 $TCID_{50}$ per cell and incubated for 1 hour at 37° C. Then, the inoculum was removed and infection medium containing the specified concentration of PDTC (0 µM to 200 µM) was added. The supernatants were removed 24 hours after infection and the viral titers (TCID) were determined in a standard plate assay.

Figure 13B:
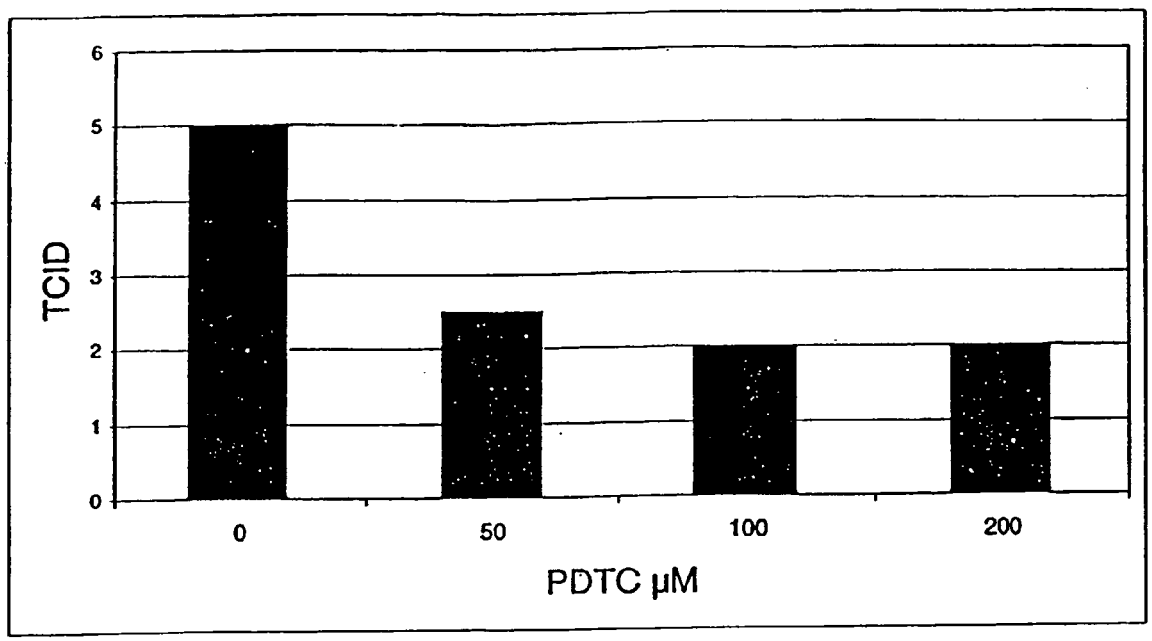

As FIG. 13B shows, the virus titer of the O-Manisa FMV virus was reduced by more than 2 log steps by PDTC, compared with the control sample (0). No PDTC was added to the control sample.

Example 13

Action of PDTC on Proliferation of FSME in Cell Culture

FSME viruses do not belong to the picornaviruses and do not cause respiratory tract disease.

Confluent monolayers of BHK-21 cells (ATCC) were infected with 10 pfu/cell of FSME virus (Neudörfel) in the presence of the following concentrations of PDTC: 1000 µM, 500 µM, 250 µM, 125 µM, 62.5 µM, 31.25 µM, 15.6 µM, 7.8 µM, 1.95 µM and 0.975 µM.

Then the cells were incubated for 4 days at 37° C., and the cell monolayer was examined microscopically. The virus proliferation was determined using an enzyme immunoassay. The microscopic examination showed no indications of toxic effects of PDTC. Quantification of the virus proliferation showed that PDTC cannot reduce the virus proliferation at any of the concentrations tested.

Similarly, we investigated whether PDTC can affect virus proliferation in suspended cells. The same concentrations as above were tested. This test, too, showed no indication of reduction of virus proliferation by PDTC.

Example 14

Action of PDTC on EMC-infected Mice

C57B16 mice were infected intraperitoneally with 10 $TCID_{50}$ of EMC virus. Then, the control group was treated intraperitoneally once daily with PBS. Two other groups were treated with 50 µl of 50 mM PDTC per day. Treatment of one group (PDTC) was started simultaneously with the infection, while treatment of the other group (PDTC 24 hpi) was started only 24 hours after the infection.

Figure 14:
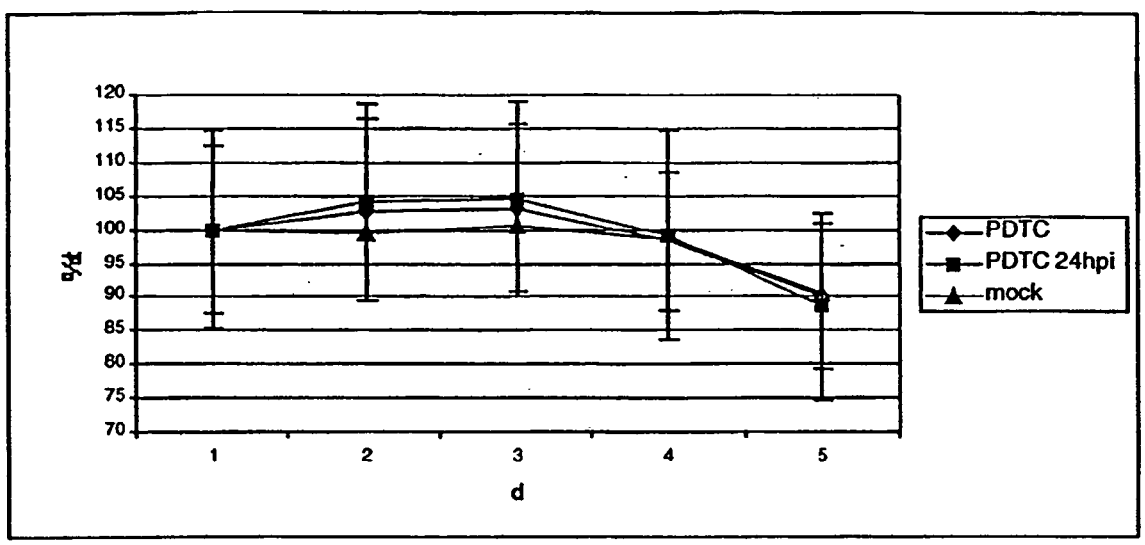
FIG. 14 shows the lack of action of PDTC against EMCV.

FIG. 14 shows the changes of the mouse weights after the beginning of the infection. It is apparent that there is no difference in treated and untreated mice. The average time to death for the infected mice was 5.5 days in every group.

This shows that PDTC has no effect on an EMC infection. EMC does indeed belong to the picorna viruses, but does not cause disease in the respiratory tract, but rather in nerve cells.

The invention claimed is:

1. A method of treating an infection by an RNA virus which attacks the respiratory tract and causes disease therein selected from the group consists of a picornavirus, orthomyxovirus, rhinovirus, enterovirus, coxsackie virus, aphthovirus, or paramyxovirus, comprising:

obtaining an agent comprising a dithiocarbamate compound having the structural formula $R_1R_2NCS_2H$, in which $R_1$ and $R_2$, independently of each other, represent a straight or branched $C_1$-$C_4$ alkyl, or, with the nitrogen atom, form an aliphatic ring with 4 to 6 C atoms or a pharmaceutically acceptable salt thereof; and administering the agent to a subject thereby treating an infection by an RNA virus which attacks the respiratory tract and causes disease therein selected from the group consists of a picornavirus, ortho-myxovirus, rhinovirus, enterovirus, coxsackie virus, aphthovirus, or paramyxovirus.

2. The method of claim 1, where in $R_1$, $R_2$, or the aliphatic ring is further defined as substituted with one or more of OH, $NO_2$, $NH_2$, COOH, SH, F, Cl, Br, I, or methyl, ethyl, or oxidized forms thereof.

3. The method of claim 1, wherein $R_1$, $R_2$, or the aliphatic ring is further defined as substituted with dimers of one or more of OH, $NO_2$, $NH_2$, COOH, SH, F, Cl, Br, I, or methyl, ethyl, or oxidized forms thereof.

4. The method of claim 1, wherein $R_1$ and $R_2$, independently of each other, represent a $C_1$-$C_3$ alkyl, or, with the nitrogen atom, form an aliphatic ring with 4 to 6 C atoms.

5. The method of claim 1, wherein the dithiocarbamate compound is pyrrolidine dithiocarbamate or N,N-diethyl dithiocarbamate.

6. The method of claim 1, wherein the infection is an infection with influenza A virus, influenza B virus, influenza C virus, parainfluenza virus, pneumovirus, human rhinovirus, equine rhinovirus, enterovirus 70, enterovirus 71, foot and mouth disease virus, or equine rhinitis virus A.

7. The method of claim 1, wherein the infection is an infection with influenza A virus.

8. The method of claim 1, wherein the dithiocarbamate compound is comprised in the agent at a concentration of from 0.01 to 5000 mM.

9. The method of claim 8, wherein the dithiocarbamate compound is comprised in the agent at a concentration of from 1 to 300 mM.

10. The method of claim 9, wherein the dithiocarbamate compound is comprised in the agent at a concentration of from 10 to 100 mM.

11. The method of claim 1, wherein the dithiocarbamate compound is comprised in the agent at a concentration of 10 mM to 1 M.

12. The method of claim 1, wherein the agent further comprises a pharmaceutically acceptable carrier.

13. The method of claim 1, wherein the agent is adapted for oral, intranasal, intravenous, rectal, parenteral, eye drop, ear drop, gargle, or aerosol administration.

14. The method of claim 1, wherein the agent comprises further antiviral substances.

15. The method of claim 1, wherein the agent comprises a combination of at least two different dithiocarbamate compounds.

16. The method of claim 1, wherein the agent comprises an antibiotic, vaccine, immune suppressant, stabilizer, immune-stimulating substance, blood product, or mixture thereof.

17. The method of claim 1, further defined as a method of inhibiting virus propagation.

* * * * *

UNITED STATES PATENT AND TRADEMARK OFFICE
CERTIFICATE OF CORRECTION

PATENT NO. : 7,282,599 B2
APPLICATION NO. : 10/483975
DATED : October 16, 2007
INVENTOR(S) : Elisabeth Gaudemak et al.

Page 1 of 1

It is certified that error appears in the above-identified patent and that said Letters Patent is hereby corrected as shown below:

Title Page, item (73), line 2, please delete "Devlopment" and insert --Development-- therefor.

Signed and Sealed this

Fifteenth Day of April, 2008

JON W. DUDAS
*Director of the United States Patent and Trademark Office*